United States Patent
Gandhi et al.

(10) Patent No.: US 11,393,597 B1
(45) Date of Patent: Jul. 19, 2022

(54) PRESCRIPTION LABEL SCANNER

(71) Applicant: Walmart Apollo, LLC, Bentonville, AR (US)

(72) Inventors: Shreyansh Prakash Gandhi, Milpitas, CA (US); Murat Yalcin, San Jose, CA (US); Stephen Richard Schmidt, Santa Clara, CA (US); Glenn Timo Werner, Bentonville, AR (US); Gina Lee, Schaumburg, IL (US); Phanindra Vuppalapati, San Jose, CA (US)

(73) Assignee: WALMART APOLLO, LLC, Bentonville, AR (US)

( * ) Notice: Subject to any disclaimer, the term of this patent is extended or adjusted under 35 U.S.C. 154(b) by 0 days.

(21) Appl. No.: 17/163,426

(22) Filed: Jan. 30, 2021

(51) Int. Cl.
*G06F 17/00* (2019.01)
*G06K 7/10* (2006.01)
*G16H 70/40* (2018.01)
*G06K 7/14* (2006.01)
*G16H 20/10* (2018.01)
*G06N 20/00* (2019.01)
*G16H 10/60* (2018.01)

(52) U.S. Cl.
CPC ......... *G16H 70/40* (2018.01); *G06K 7/10861* (2013.01); *G06K 7/1443* (2013.01); *G06K 7/1482* (2013.01); *G06N 20/00* (2019.01); *G16H 20/10* (2018.01); *G06K 2007/10504* (2013.01); *G16H 10/60* (2018.01)

(58) Field of Classification Search
CPC .... G16H 70/40; G16H 20/10; G06K 7/10861; G06K 7/1443; G06K 7/1482; G06K 2007/10504
USPC .................................................. 235/375, 470
See application file for complete search history.

(56) References Cited

U.S. PATENT DOCUMENTS

| | | | |
|---|---|---|---|
| 4,044,227 A | * | 8/1977 | Holm .................. G06K 7/1092 209/583 |
| 7,774,097 B2 | | 8/2010 | Rosenblum |
| | | | (Continued) |

OTHER PUBLICATIONS

"Camera-Based Document Analysis and Recognition," Proceedings of the Second International Workshop on Camera-Based Document Analysis and Recognition, edited by K. Kise and D. S. Doermann Sep. 22, 2007.

*Primary Examiner* — Jamara A Franklin
(74) *Attorney, Agent, or Firm* — Bryan Cave Leighton Paisner LLP

(57) ABSTRACT

A system including one or more processors and one or more non-transitory computer-readable media storing computing instructions configured to run on the one or more processors and perform facilitating display of instructions to a user interface of a mobile device of a user on how to rotate a medication package in front of a camera of the mobile device to capture a video of a rotated view of a non-planar surface of the medication package; capturing, using the camera, the video of the rotated view of the non-planar surface; generating, using an input pre-processing algorithm, a series of images from the video; recognizing, using an output post-processing algorithm, respective words from the respective machine-readable text data; merging, using a merging algorithm, the respective words from the images to create lines of text; and extracting, using a machine learning algorithm, prescription data associated with prescription data fields from the lines of text. Other embodiments are described.

20 Claims, 26 Drawing Sheets

(56) References Cited

U.S. PATENT DOCUMENTS

| | | |
|---|---|---|
| 8,208,729 B2 | 6/2012 | Foss |
| 9,251,413 B2 | 2/2016 | Meier et al. |
| 10,397,432 B2 | 8/2019 | Naaman |
| 2003/0214129 A1* | 11/2003 | Adler ................. A61J 7/04 283/81 |
| 2008/0056556 A1* | 3/2008 | Eller ............... G07F 17/0092 382/142 |
| 2008/0306787 A1 | 12/2008 | Hamilton et al. |
| 2009/0196485 A1 | 8/2009 | Mueller et al. |
| 2011/0202366 A1 | 8/2011 | Akers et al. |
| 2012/0330665 A1* | 12/2012 | Berkun ............... G06V 30/412 235/494 |
| 2013/0197693 A1 | 8/2013 | Kamen et al. |
| 2013/0208084 A1 | 8/2013 | Brunner et al. |
| 2016/0267357 A1 | 9/2016 | Smith et al. |
| 2018/0199065 A1 | 7/2018 | Adams et al. |
| 2018/0366218 A1 | 12/2018 | Smith et al. |

* cited by examiner

401

| 501 — Upon initiating the camera on the mobile device of the user, triggering a window interface to appear on the user interface of the mobile device |

| 502 — Upon sensing that the camera is pointed at the medication package, automatically triggering an image box with instructions to rotate the medication package |

403

| 601 – Mapping light and dark areas, using image inversion, to create a digital negative |

| 602 – Adding, using dilation image processing, first pixels to outer borders |

| 603 – Removing, using erosion image processing, second pixels from the outer borders |

| 604 – Modifying, using image rescaling, a size of the image to a different scale |

| 605 – Assigning a thresholding value to pixels of the image |

| 606 – Partitioning the image using image binarization processing to detect grey scale values |

| 607 – Defining borders of the image |

| 608 – Rotating the image |

| 609 – Deskewing the image to align the image horizontally and vertically |

| 610 – De-warping the image to remove warp distortion of the image |

| 801 – Receiving lines of text outputted by the merging algorithm |

| 802 – Extracting, using a machine learning algorithm, prescription data from the lines of text |

| 803 – Populating each data field of prescription data fields with prescription data |

PRESCRIPTION LABEL SCANNER

TECHNICAL FIELD

This disclosure relates generally relates to a prescription label scanner.

BACKGROUND

Often a single user can be prescribed multiple prescriptions over a period of time. Such a list of medications can be prescribed from different health providers or filled by different pharmacies. Portions of prescription labels placed over a curved surface of a medication package can be obscured or illegible. Such prescription data can be challenging to accurately and efficiently track when using a camera to capture the data.

BRIEF DESCRIPTION OF THE DRAWINGS

To facilitate further description of the embodiments, the following drawings are provided in which:

FIG. 6 shows an embodiment of activity of FIG. 4 of generating, using an input pre-processing algorithm, a series of images from the video, wherein each of the images shows a respective portion of the non-planar surface;

FIG. 8 shows an embodiment of activity of FIG. 4 of extracting, using a machine learning algorithm, prescription data associated with prescription data fields from the lines of text;

FIG. 21 illustrates a set of images used and/or created in image pre-processing techniques, such as defining borders;

FIG. 22 illustrates a set of images used and/or created in image processing techniques, such as deskewing;

Figure 1:
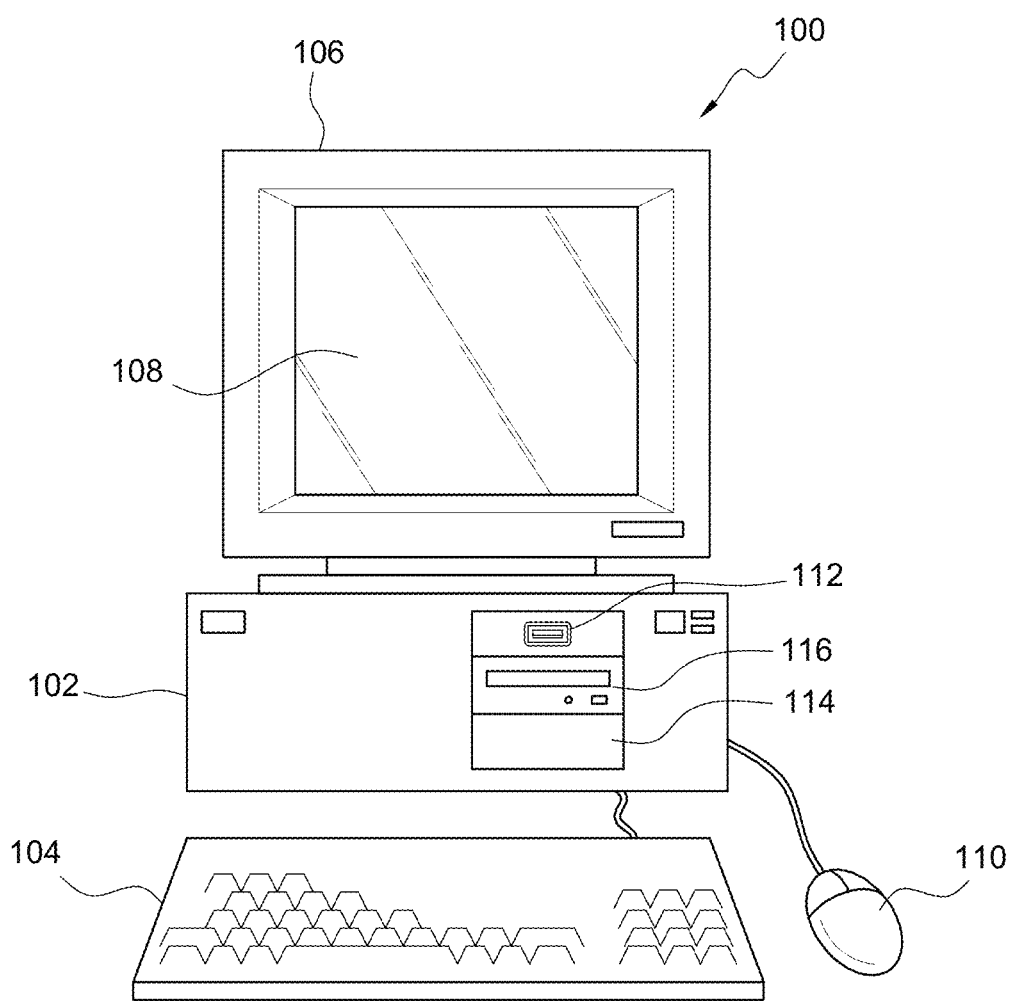
FIG. 1 illustrates a front elevational view of a computer system that is suitable for implementing an embodiment of the system disclosed in FIG. 3.

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

The terms "couple," "coupled," "couples," "coupling," and the like should be broadly understood and refer to connecting two or more elements mechanically and/or otherwise. Two or more electrical elements may be electrically coupled together, but not be mechanically or otherwise coupled together. Coupling may be for any length of time, e.g., permanent or semi-permanent or only for an instant. "Electrical coupling" and the like should be broadly understood and include electrical coupling of all types. The absence of the word "removably," "removable," and the like near the word "coupled," and the like does not mean that the coupling, etc. in question is or is not removable.

As defined herein, two or more elements are "integral" if they are comprised of the same piece of material. As defined herein, two or more elements are "non-integral" if each is comprised of a different piece of material.

As defined herein, "approximately" can, in some embodiments, mean within plus or minus ten percent of the stated value. In other embodiments, "approximately" can mean within plus or minus five percent of the stated value. In further embodiments, "approximately" can mean within plus or minus three percent of the stated value. In yet other embodiments, "approximately" can mean within plus or minus one percent of the stated value.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real-time" encompasses operations that occur in "near" real-time or somewhat delayed from a triggering event. In a number of embodiments, "real-time" can mean real-time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than 1 second (ms), 10 ms, 50 ms, 100 ms, 500 ms, or 1 second

DESCRIPTION OF EXAMPLES OF EMBODIMENTS

In many embodiments, prescription label scanner can be used to generate prescription data of a user from a prescription label to create a record and/or a database for a user, such a record can include a health record, a medical record, and/or another suitable type of record. Such a record can be transmitted and/or shared electronically to multiple third parties and/or multiple third party vendors by the user via a network (e.g., the Internet).

Figure 2:
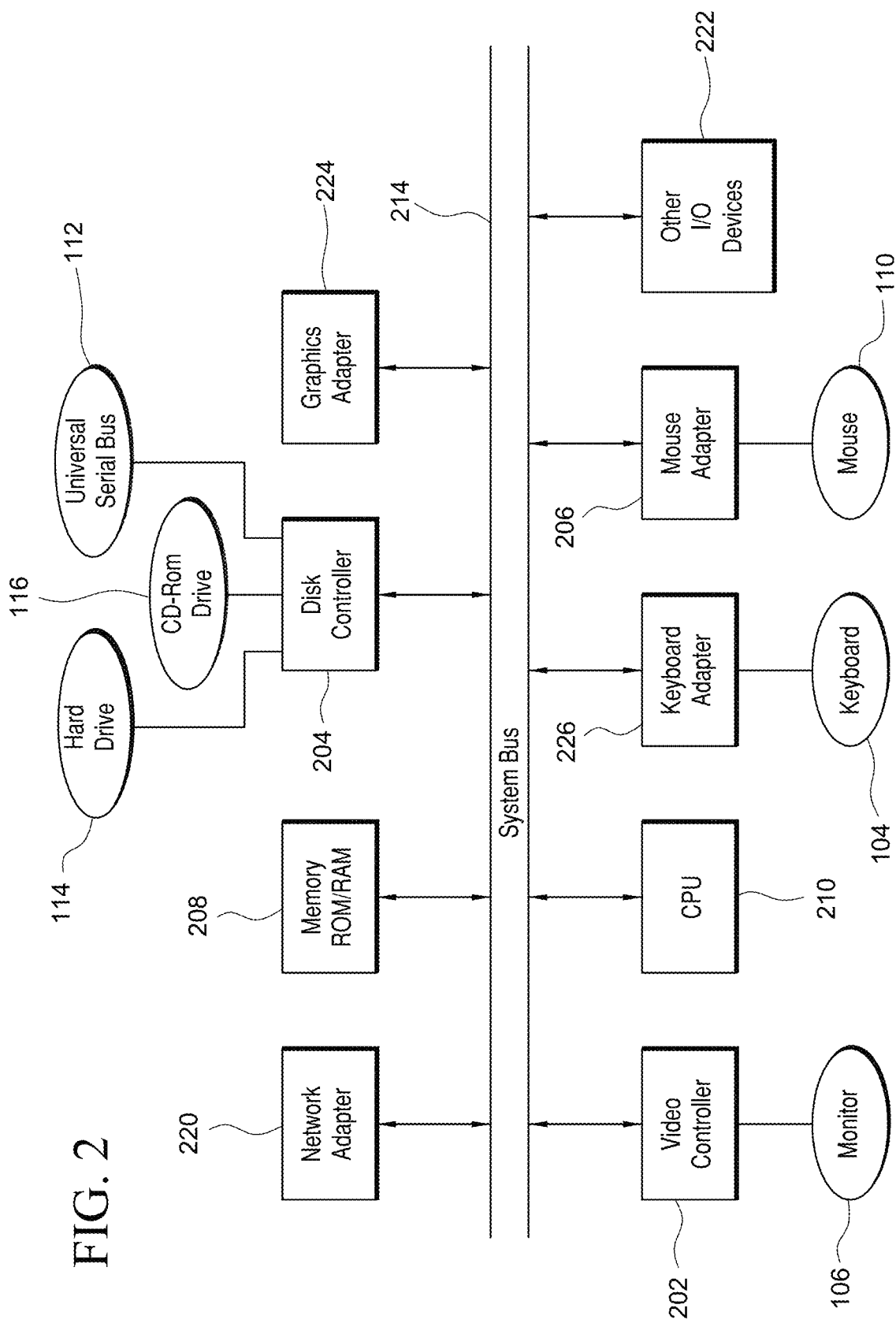
FIG. 2 illustrates a representative block diagram of an example of the elements included in the circuit boards inside a chassis of the computer system of FIG. 1.

Turning to the drawings, FIG. 1 illustrates an exemplary embodiment of a computer system 100, all of which or a portion of which can be suitable for (i) implementing part or all of one or more embodiments of the techniques, methods, and systems and/or (ii) implementing and/or operating part or all of one or more embodiments of the non-transitory computer readable media described herein. As an example, a different or separate one of computer system 100 (and its internal components, or one or more elements of computer system 100) can be suitable for implementing part or all of the techniques described herein. Computer system 100 can comprise chassis 102 containing one or more circuit boards (not shown), a Universal Serial Bus (USB) port 112, a Compact Disc Read-Only Memory (CD-ROM) and/or Digital Video Disc (DVD) drive 116, and a hard drive 114. A representative block diagram of the elements included on the circuit boards inside chassis 102 is shown in FIG. 2. A central processing unit (CPU) 210 in FIG. 2 is coupled to a system bus 214 in FIG. 2. In various embodiments, the architecture of CPU 210 can be compliant with any of a variety of commercially distributed architecture families.

Continuing with FIG. 2, system bus 214 also is coupled to memory storage unit 208 that includes both read only memory (ROM) and random access memory (RAM). Non-volatile portions of memory storage unit 208 or the ROM can be encoded with a boot code sequence suitable for restoring computer system 100 (FIG. 1) to a functional state after a system reset. In addition, memory storage unit 208 can include microcode such as a Basic Input-Output System (BIOS). In some examples, the one or more memory storage units of the various embodiments disclosed herein can include memory storage unit 208, a USB-equipped electronic device (e.g., an external memory storage unit (not shown) coupled to universal serial bus (USB) port 112 (FIGS. 1-2)), hard drive 114 (FIGS. 1-2), and/or CD-ROM, DVD, Blu-Ray, or other suitable media, such as media configured to be used in CD-ROM and/or DVD drive 116 (FIGS. 1-2). Non-volatile or non-transitory memory storage unit(s) refer to the portions of the memory storage units(s) that are non-volatile memory and not a transitory signal. In the same or different examples, the one or more memory storage units of the various embodiments disclosed herein can include an operating system, which can be a software program that manages the hardware and software resources of a computer and/or a computer network. The operating system can perform basic tasks such as, for example, controlling and allocating memory, prioritizing the processing of instructions, controlling input and output devices, facilitating networking, and managing files. Exemplary operating systems can include one or more of the following: (i) Microsoft® Windows® operating system (OS) by Microsoft Corp. of Redmond, Wash., United States of America, (ii) Mac® OS X by Apple Inc. of Cupertino, Calif., United States of America, (iii) UNIX® OS, and (iv) Linux® OS. Further exemplary operating systems can comprise one of the following: (i) the iOS® operating system by Apple Inc. of Cupertino, Calif., United States of America, (ii) the Blackberry® operating system by Research In Motion (RIM) of Waterloo, Ontario, Canada, (iii) the WebOS operating system by LG Electronics of Seoul, South Korea, (iv) the Android™ operating system developed by Google, of Mountain View, Calif., United States of America, (v) the Windows Mobile™ operating system by Microsoft Corp. of Redmond, Wash., United States of America, or (vi) the Symbian™ operating system by Accenture PLC of Dublin, Ireland.

As used herein, "processor" and/or "processing module" means any type of computational circuit, such as but not limited to a microprocessor, a microcontroller, a controller, a complex instruction set computing (CISC) microprocessor, a reduced instruction set computing (RISC) microprocessor, a very long instruction word (VLIW) microprocessor, a graphics processor, a digital signal processor, or any other type of processor or processing circuit capable of performing the desired functions. In some examples, the one or more processors of the various embodiments disclosed herein can comprise CPU 210.

In the depicted embodiment of FIG. 2, various I/O devices such as a disk controller 204, a graphics adapter 224, a video controller 202, a keyboard adapter 226, a mouse adapter 206, a network adapter 220, and other I/O devices 222 can be coupled to system bus 214. Keyboard adapter 226 and mouse adapter 206 are coupled to a keyboard 104 (FIGS. 1-2) and a mouse 110 (FIGS. 1-2), respectively, of computer system 100 (FIG. 1). While graphics adapter 224 and video controller 202 are indicated as distinct units in FIG. 2, video controller 202 can be integrated into graphics adapter 224, or vice versa in other embodiments. Video controller 202 is suitable for refreshing a monitor 106 (FIGS. 1-2) to display images on a screen 108 (FIG. 1) of computer system 100 (FIG. 1). Disk controller 204 can control hard drive 114 (FIGS. 1-2), USB port 112 (FIGS. 1-2), and CD-ROM and/or DVD drive 116 (FIGS. 1-2). In other embodiments, distinct units can be used to control each of these devices separately.

In some embodiments, network adapter 220 can comprise and/or be implemented as a WNIC (wireless network interface controller) card (not shown) plugged or coupled to an expansion port (not shown) in computer system 100 (FIG. 1). In other embodiments, the WNIC card can be a wireless network card built into computer system 100 (FIG. 1). A wireless network adapter can be built into computer system 100 (FIG. 1) by having wireless communication capabilities integrated into the motherboard chipset (not shown), or implemented via one or more dedicated wireless communication chips (not shown), connected through a PCI (peripheral component interconnector) or a PCI express bus of computer system 100 (FIG. 1) or USB port 112 (FIG. 1). In other embodiments, network adapter 220 can comprise and/or be implemented as a wired network interface controller card (not shown).

Although many other components of computer system 100 (FIG. 1) are not shown, such components and their interconnection are well known to those of ordinary skill in the art. Accordingly, further details concerning the construction and composition of computer system 100 (FIG. 1) and the circuit boards inside chassis 102 (FIG. 1) are not discussed herein.

When computer system 100 in FIG. 1 is running, program instructions stored on a USB drive in USB port 112, on a CD-ROM or DVD in CD-ROM and/or DVD drive 116, on hard drive 114, or in memory storage unit 208 (FIG. 2) are executed by CPU 210 (FIG. 2). A portion of the program instructions, stored on these devices, can be suitable for carrying out all or at least part of the techniques described herein. In various embodiments, computer system 100 can be reprogrammed with one or more modules, system, applications, and/or databases, such as those described herein, to convert a general purpose computer to a special purpose computer. For purposes of illustration, programs and other executable program components are shown herein as discrete systems, although it is understood that such programs and components may reside at various times in different storage components of computing device 100, and can be executed by CPU 210. Alternatively, or in addition to, the systems and procedures described herein can be implemented in hardware, or a combination of hardware, software, and/or firmware. For example, one or more application specific integrated circuits (ASICs) can be programmed to carry out one or more of the systems and procedures described herein. For example, one or more of the programs and/or executable program components described herein can be implemented in one or more ASICs.

Although computer system 100 is illustrated as a desktop computer in FIG. 1, there can be examples where computer system 100 may take a different form factor while still having functional elements similar to those described for computer system 100. In some embodiments, computer system 100 may comprise a single computer, a single server, or a cluster or collection of computers or servers, or a cloud of computers or servers. Typically, a cluster or collection of servers can be used when the demand on computer system 100 exceeds the reasonable capability of a single server or computer. In certain embodiments, computer system 100 may comprise a portable computer, such as a laptop computer. In certain other embodiments, computer system 100 may comprise a mobile device, such as a smartphone. In certain additional embodiments, computer system 100 may comprise an embedded system.

Figure 3:
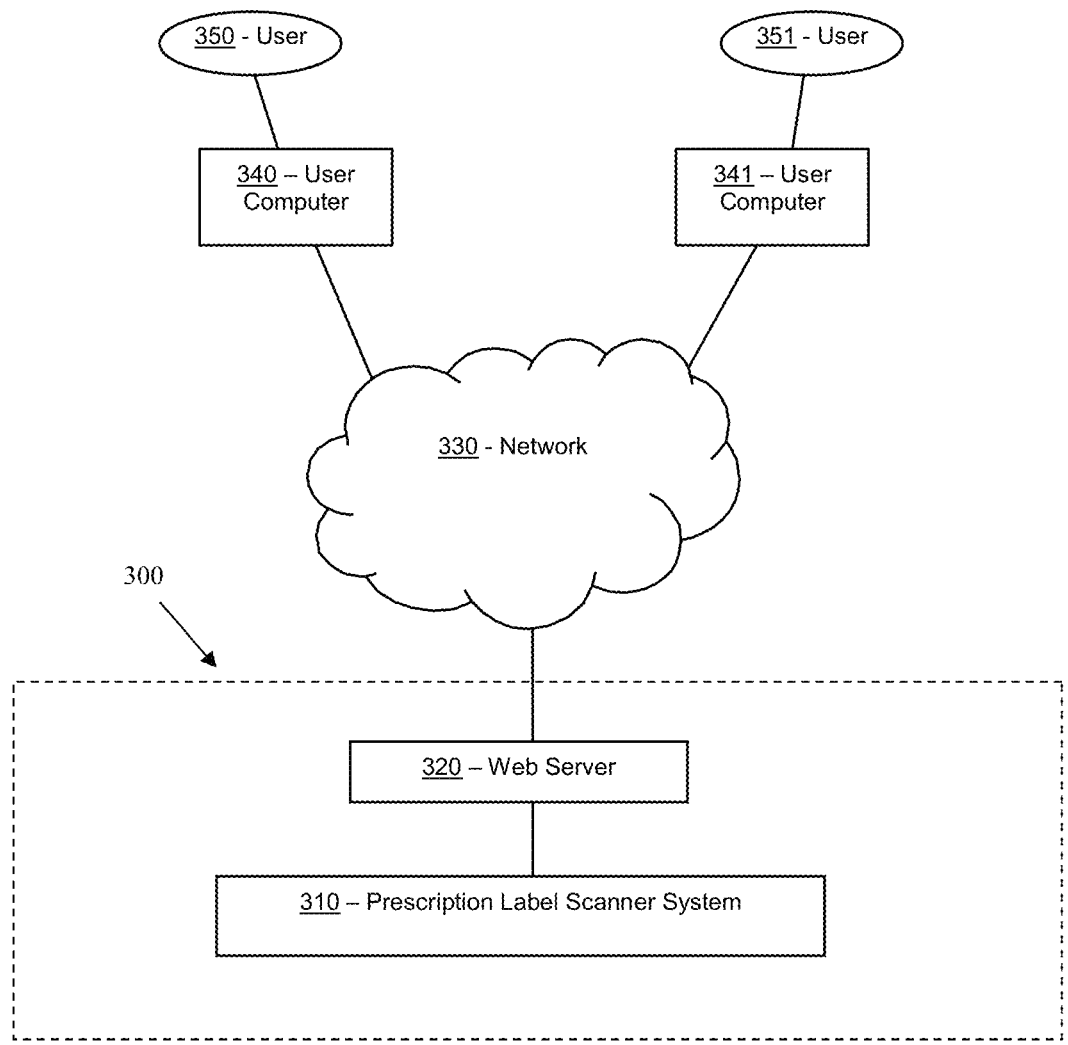
FIG. 3 illustrates a block diagram of a system that can be employed for extracting prescription information of a user by using a prescription label scanner, according to an embodiment.

Turning ahead in the drawings, FIG. 3 illustrates a block diagram of a system 300 that can be employed for extracting prescription information of a user by using a prescription label scanner. System 300 is merely exemplary and embodiments of the system are not limited to the embodiments presented herein. The system can be employed in many different embodiments or examples not specifically depicted or described herein. In some embodiments, certain elements, modules, or systems of system 300 can perform various procedures, processes, and/or activities. In other embodiments, the procedures, processes, and/or activities can be performed by other suitable elements, modules, or systems of system 300. System 300 can be implemented with hardware and/or software, as described herein. In some embodiments, part or all of the hardware and/or software can be conventional, while in these or other embodiments, part or all of the hardware and/or software can be customized (e.g., optimized) for implementing part or all of the functionality of system 300 described herein.

In many embodiments, system 300 can include a prescription label scanner system 310 and/or a web server 320. Prescription label scanner system 310 and/or web server 320 can each be a computer system, such as computer system 100 (FIG. 1), as described above, and can each be a single computer, a single server, or a cluster or collection of computers or servers, or a cloud of computers or servers. In another embodiment, a single computer system can host two or more of, or all of, prescription label scanner system 310 and/or web server 320. Additional details regarding prescription label scanner system 310 and/or web server 320 are described herein.

In a number of embodiments, each of prescription label scanner system 310 and/or web server 320 can be a special-purpose computer programed specifically to perform specific functions not associated with a general-purpose computer, as described in greater detail below. Also, although not shown in the drawings, in some embodiments, prescription label scanner system 310 can include webserver 320.

In some embodiments, web server 320 can be in data communication through a network 330 with one or more user computers, such as user computers 340 and/or 341. Network 330 can be a public network (e.g., the Internet), a private network or a hybrid network. In some embodiments, user computers 340-341 can be used by users, such as users 350 and 351, which also can be referred to as customers, patients, caregivers, legal guardians, and/or legal representatives of the patient, in which case, user computers 340 and 341 can be referred to as customer computers. The terms user, customers, patients, caregivers, legal guardians, legal representatives, and/or another suitable user can be used interchangeably under suitable and/or appropriate circumstances. In many embodiments, web server 320 can host one or more sites (e.g., websites) that allow users to browse and/or search for prescription data (e.g., prescriptions) of prescription labels, to extract data within data fields and/or text boxes of the prescription labels, and/or to order (e.g., purchase) prescription refills, in addition to other suitable activities associated with the prescription label.

In some embodiments, an internal network that is not open to the public can be used for communications between prescription label scanner system 310 and/or web server 320 within system 300. Accordingly, in some embodiments, prescription label scanner system 310 (and/or the software used by such systems) can refer to a back end of system 300, which can be operated by an operator and/or administrator of system 300, and web server 320 (and/or the software used by such system) can refer to a front end of system 300, and can be accessed and/or used by one or more users, such as users 350-351, using user computers 340-341, respectively. In these or other embodiments, the operator and/or administrator of system 300 can manage system 300, the processor(s) of system 300, and/or the memory storage unit(s) of system 300 using the input device(s) and/or display device(s) of system 300.

In certain embodiments, user computers 340-341 can be desktop computers, laptop computers, a mobile device, and/or other endpoint devices used by one or more users 350 and 351, respectively. A mobile device can refer to a portable electronic device (e.g., an electronic device easily conveyable by hand by a person of average size) with the capability to present audio and/or visual data (e.g., text, images, videos, music, etc.). For example, a mobile device can include at least one of a digital media player, a cellular telephone (e.g., a smartphone), a personal digital assistant, a handheld digital computer device (e.g., a tablet personal computer device), a laptop computer device (e.g., a notebook computer device, a netbook computer device), a wearable user computer device, or another portable computer device with the capability to present audio and/or visual data (e.g., images, videos, music, etc.). Thus, in many examples, a mobile device can include a volume and/or weight sufficiently small as to permit the mobile device to be easily conveyable by hand. For examples, in some embodiments, a mobile device can occupy a volume of less than or equal to approximately 1790 cubic centimeters, 2434 cubic centimeters, 2876 cubic centimeters, 4056 cubic centimeters, and/or 5752 cubic centimeters. Further, in these embodiments, a mobile device can weigh less than or equal to 15.6 Newtons, 17.8 Newtons, 22.3 Newtons, 31.2 Newtons, and/or 44.5 Newtons.

Exemplary mobile devices can include (i) an iPod®, iPhone®, iTouch®, iPad®, MacBook® or similar product by Apple Inc. of Cupertino, Calif., United States of America, (ii) a Blackberry® or similar product by Research in Motion (RIM) of Waterloo, Ontario, Canada, (iii) a Lumia® or similar product by the Nokia Corporation of Keilaniemi, Espoo, Finland, and/or (iv) a Galaxy™ or similar product by the Samsung Group of Samsung Town, Seoul, South Korea. Further, in the same or different embodiments, a mobile device can include an electronic device configured to implement one or more of (i) the iPhone® operating system by Apple Inc. of Cupertino, Calif., United States of America, (ii) the Blackberry® operating system by Research In Motion (RIM) of Waterloo, Ontario, Canada, (iii) the Palm® operating system by Palm, Inc. of Sunnyvale, Calif., United States, (iv) the Android™ operating system developed by the Open Handset Alliance, (v) the Windows Mobile™ operating system by Microsoft Corp. of Redmond, Wash., United States of America, or (vi) the Symbian™ operating system by Nokia Corp. of Keilaniemi, Espoo, Finland.

Further still, the term "wearable user computer device" as used herein can refer to an electronic device with the capability to present audio and/or visual data (e.g., text, images, videos, music, etc.) that is configured to be worn by a user and/or mountable (e.g., fixed) on the user of the wearable user computer device (e.g., sometimes under or over clothing; and/or sometimes integrated with and/or as clothing and/or another accessory, such as, for example, a hat, eyeglasses, a wrist watch, shoes, etc.). In many examples, a wearable user computer device can include a mobile device, and vice versa. However, a wearable user computer device does not necessarily include a mobile device, and vice versa.

In specific examples, a wearable user computer device can include a head mountable wearable user computer device (e.g., one or more head mountable displays, one or more eyeglasses, one or more contact lenses, one or more retinal displays, etc.) or a limb mountable wearable user computer device (e.g., a smart watch). In these examples, a head mountable wearable user computer device can be mountable in close proximity to one or both eyes of a user of the head mountable wearable user computer device and/or vectored in alignment with a field of view of the user.

In more specific examples, a head mountable wearable user computer device can include (i) Google Glass™ product or a similar product by Google Inc. of Menlo Park, Calif., United States of America; (ii) the Eye Tap™ product, the Laser Eye Tap™ product, or a similar product by ePI Lab of Toronto, Ontario, Canada, and/or (iii) the Raptyr™ product, the STAR 1200™ product, the Vuzix Smart Glasses M100™ product, or a similar product by Vuzix Corporation of Rochester, N.Y., United States of America. In other specific examples, a head mountable wearable user computer device can include the Virtual Retinal Display™ product, or similar product by the University of Washington of Seattle, Wash., United States of America. Meanwhile, in further specific examples, a limb mountable wearable user computer device can include the iWatch™ product, or similar product by Apple Inc. of Cupertino, Calif., United States of America, the Galaxy Gear or similar product of Samsung Group of Samsung Town, Seoul, South Korea, the Moto 360 product or similar product of Motorola of Schaumburg, Ill., United States of America, and/or the Zip™ product, One™ product, Flex™ product, Charge™ product, Surge™ product, or similar product by Fitbit Inc. of San Francisco, Calif., United States of America.

In many embodiments, prescription label scanner system 310 and/or web server 320 can each include one or more input devices (e.g., one or more keyboards, one or more keypads, one or more pointing devices such as a computer mouse or computer mice, one or more touchscreen displays, a microphone, etc.), and/or can each include one or more display devices (e.g., one or more monitors, one or more touch screen displays, projectors, etc.). In these or other embodiments, one or more of the input device(s) can be similar or identical to keyboard 104 (FIG. 1) and/or a mouse 110 (FIG. 1). Further, one or more of the display device(s) can be similar or identical to monitor 106 (FIG. 1) and/or screen 108 (FIG. 1). The input device(s) and the display device(s) can be coupled to prescription label scanner system 310 and/or web server 320, in a wired manner and/or a wireless manner, and the coupling can be direct and/or indirect, as well as locally and/or remotely. As an example of an indirect manner (which may or may not also be a remote manner), a keyboard-video-mouse (KVM) switch can be used to couple the input device(s) and the display device(s) to the processor(s) and/or the memory storage unit(s). In some embodiments, the KVM switch also can be part of prescription label scanner system 310 and/or web server 320. In a similar manner, the processors and/or the non-transitory computer-readable media can be local and/or remote to each other.

Meanwhile, in many embodiments, prescription label scanner system 310 and/or web server 320 also can be configured to communicate with and/or include one or more databases and/or other suitable databases. The one or more databases can include an item database that contains information about items or SKUs (stock keeping units), for example, among other data as described herein. The one or more databases can be stored on one or more memory storage units (e.g., non-transitory computer readable media), which can be similar or identical to the one or more memory storage units (e.g., non-transitory computer readable media) described above with respect to computer system 100 (FIG. 1). Also, in some embodiments, for any particular database of the one or more databases, that particular database can be stored on a single memory storage unit, or the contents of that particular database can be spread across multiple ones of the memory storage units storing the one or more databases, depending on the size of the particular database and/or the storage capacity of the memory storage units.

The one or more databases can each include a structured (e.g., indexed) collection of data and can be managed by any suitable database management systems configured to define, create, query, organize, update, and manage database(s). Exemplary database management systems can include MySQL (Structured Query Language) Database, PostgreSQL Database, Microsoft SQL Server Database, Oracle Database, SAP (Systems, Applications, & Products) Database, and IBM DB2 Database.

Meanwhile, communication between prescription label scanner system 310 and/or web server 320, and/or the one or more databases, can be implemented using any suitable manner of wired and/or wireless communication. Accordingly, system 300 can include any software and/or hardware components configured to implement the wired and/or wireless communication. Further, the wired and/or wireless communication can be implemented using any one or any combination of wired and/or wireless communication (e.g., ring, line, tree, bus, mesh, star, daisy chain, hybrid, etc.) and/or protocols (e.g., personal area network (PAN) protocol(s), local area network (LAN) protocol(s), wide area network (WAN) protocol(s), cellular network protocol(s), powerline network protocol(s), etc.). Exemplary PAN protocol(s) can include Bluetooth, Zigbee, Wireless Universal Serial Bus (USB), Z-Wave, etc.; exemplary LAN and/or WAN protocol(s) can include Institute of Electrical and Electronic Engineers (IEEE) 802.3 (also known as Ethernet), IEEE 802.11 (also known as WiFi), etc.; and exemplary wireless cellular network protocol(s) can include Global System for Mobile Communications (GSM), General Packet Radio Service (GPRS), Code Division Multiple Access (CDMA), Evolution-Data Optimized (EV-DO), Enhanced Data Rates for GSM Evolution (EDGE), Universal Mobile Telecommunications System (UMTS), Digital Enhanced Cordless Telecommunications (DECT), Digital AMPS (IS-136/Time Division Multiple Access (TDMA)), Integrated Digital Enhanced Network (iDEN), Evolved High-Speed Packet Access (HSPA+), Long-Term Evolution (LTE), WiMAX, etc. The specific communication software and/or hardware implemented can depend on the network topologies and/or protocols implemented, and vice versa. In many embodiments, exemplary communication hardware can include wired communication hardware including, for example, one or more data buses, such as, for example, universal serial bus(es), one or more networking cables, such as, for example, coaxial cable(s), optical fiber cable(s), and/or twisted pair cable(s), any other suitable data cable, etc. Further exemplary communication hardware can include wireless communication hardware including, for example, one or more radio transceivers, one or more infrared transceivers, etc. Additional exemplary communication hardware can include one or more networking components (e.g., modulator-demodulator components, gateway components, etc.).

In some embodiments, prescription label scanner system 310 can be a general-purpose computer or a special-purpose computer programmed to perform specific functions and/or applications.

Figure 4:
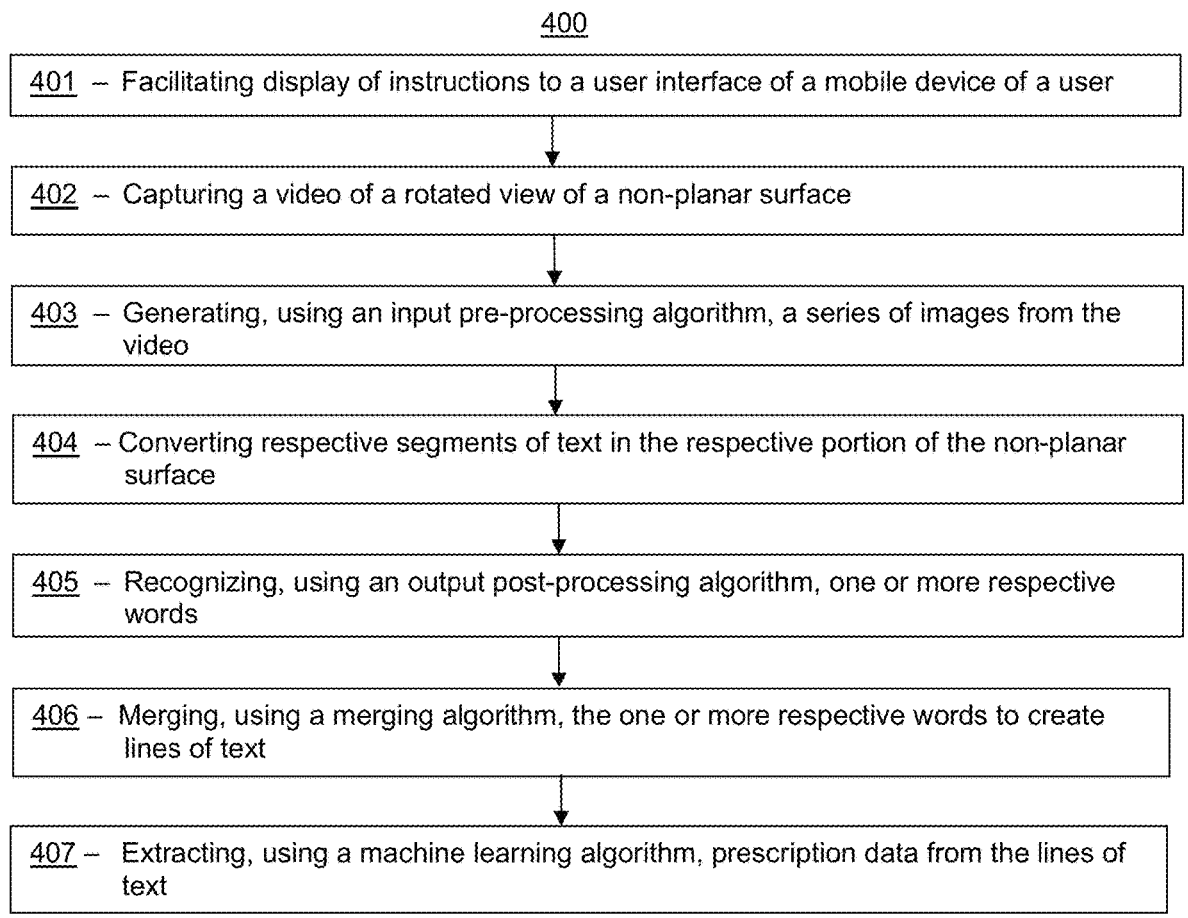
FIG. 4 illustrates a flow chart for a method, according to another embodiment.

Turning ahead in the drawings, FIG. 4 illustrates a flow chart for a method 400, according to another embodiment. In some embodiments, method 400 can be a method of extracting prescription data from a prescription label attached to a medication package, where the surface of the medication package can include (i) a planar surface and/or (ii) a non-planar surface. Method 400 is merely exemplary and is not limited to the embodiments presented herein. Method 400 can be employed in many different embodiments and/or examples not specifically depicted or described herein. In some embodiments, the procedures, the processes, and/or the activities of method 400 can be performed in the order presented. In other embodiments, the procedures, the processes, and/or the activities of method 400 can be performed in any suitable order. In still other embodiments, one or more of the procedures, the processes, and/or the activities of method 400 can be combined or skipped. In several embodiments, system 300 (FIG. 3) can be suitable to perform method 400 and/or one or more of the activities of method 400.

In these or other embodiments, one or more of the activities of method 400 can be implemented as one or more computing instructions configured to run at one or more processors and configured to be stored at one or more non-transitory computer-readable media. Such non-transitory computer-readable media can be part of a computer system such as prescription label scanner system 310 and/or web server 320. The processor(s) can be similar or identical to the processor(s) described above with respect to computer system 100 (FIG. 1).

Referring to FIG. 4, method 400 can include an activity 401 of facilitating display of instructions to a user interface of a mobile device of a user on how to rotate a medication package in front of a camera of the mobile device to capture a video of a rotated view of a non-planar surface of the medication package. In some embodiments, a label with a prescription for a medication can be affixed to the medication package, such a label can include a variety of formats and types of labels particular to a medication type and/or retail store (e.g., pharmacy). In various embodiments, a medication package can include a variety of types of containers and/or shapes of containers, such as a rounded bottle, a liquid dispenser, a tube, a box, an aerosol, a pump dispenser, and/or another suitable type of medication package.

In various embodiments, the user and/or another suitable person can rotate the medication package in front of the camera lens while the camera of the mobile device remains in a stationary position. In a number of embodiments, by viewing the user interface of the mobile device while the camera lens is aimed at the medication package, the user can concurrently monitor (e.g., view) the position of the medication package. In some embodiments, the instructions and/or recommendations can be displayed on the user interface at particular time periods, such time periods can include (i) prior to operating the camera and/or (ii) during the operation of the camera.

Figure 12:
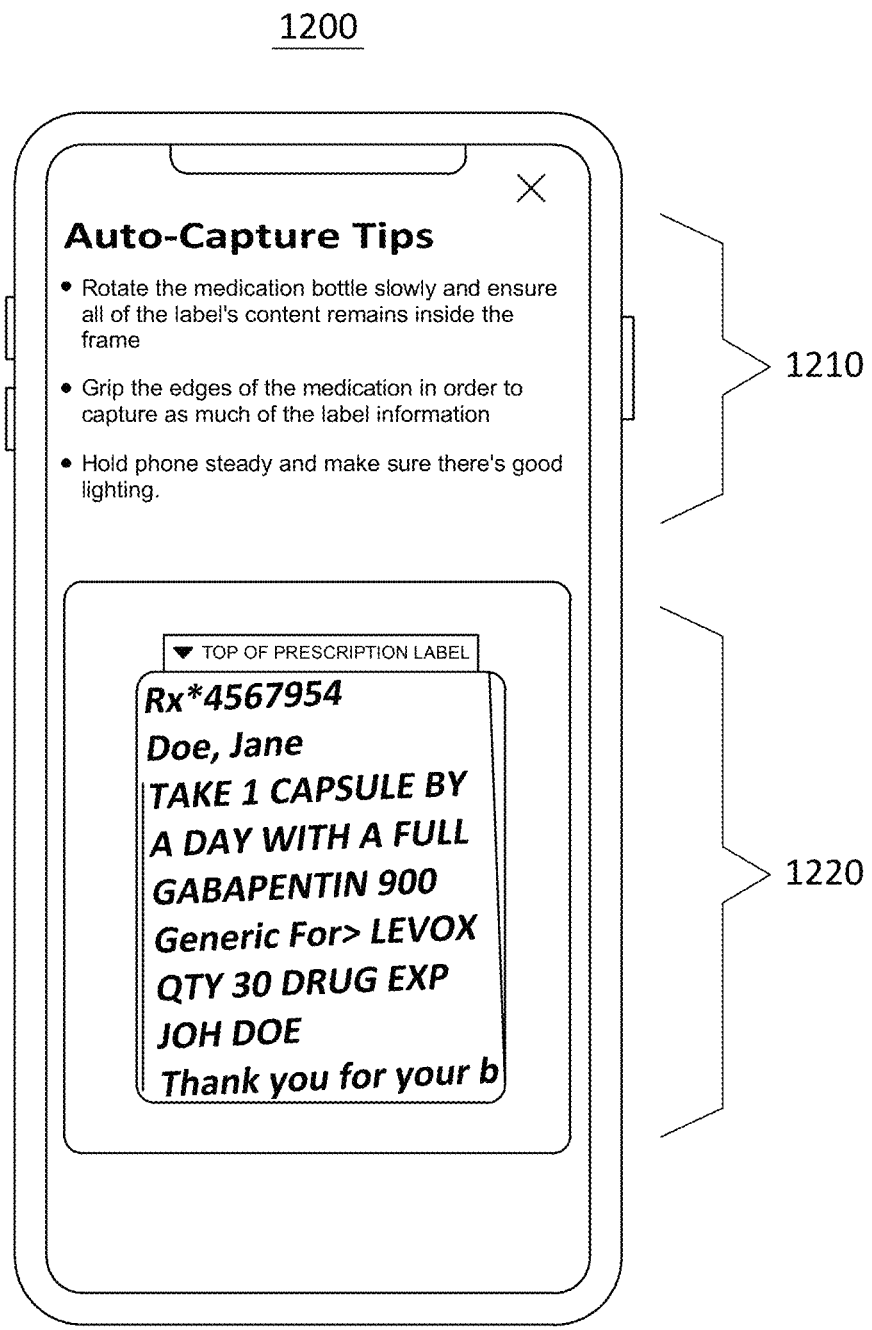
FIG. 12 illustrates an exemplary user interface display, according to an embodiment.

In several embodiments, one or more sensors in the camera can monitor one or more conditions during the process, such as lighting conditions, a position of the medication package as lined up with the camera lens, and/or another suitable condition associated with the process. Based on the activity detected by the sensors in the camera, the system can generate instructions and/or recommendations to display to the user including (i) a corrective action, or (ii) a modification of a position of the medication package as viewed through the camera lens. Such a corrective action displayed on the user interface can include a notification to the user, such as, whether adequate lighting exists, whether the medication package should be moved to (i) a different location, (ii) a different position, and/or another suitable corrective instruction. For example, instructions and/or recommendations can include: a notification to the user that the targeted view of the label as visualized through the camera lens is not optimally aligned as to capture all of the targeted information on the label, a command to change or adjust environmental conditions (e.g., light) prior to capturing the targeted information on the label, a recommendation to move the targeted medication package in a particular manner, a suggestion to modify the speed at which the medication package is being rotated while operating the camera, and/or another suitable instruction to assist to user. Such instructions and/or recommendations displayed on the user interface can be similar or identical to the instructions and/or recommendations described below in connection with exemplary use interface display 1200 (FIG. 12).

Figure 5:
FIG. 5 shows an embodiment of activity of FIG. 4 of facilitating display of instructions to a user interface of a mobile device of a user on how to rotate a medication package in front of a camera of the mobile device to capture a video of a rotated view of a non-planar surface of the medication package.

Turning ahead in the drawings, FIG. 5 illustrates a flow chart for activity 401 of facilitating display of instructions to a user interface of a mobile device of a user on how to rotate a medication package in front of a camera of the mobile device to capture a video of a rotated view of a non-planar surface of the medication package, according to an embodiment. Activity 401 is merely exemplary and is not limited to the embodiments presented herein. Activity 401 can be employed in many different embodiments and/or examples not specifically depicted or described herein. In some embodiments, the procedures, the processes, and/or the activities of activity 401 can be performed in the order presented. In other embodiments, the procedures, the processes, and/or the activities of activity 401 can be performed in any suitable order. In still other embodiments, one or more of the procedures, the processes, and/or the activities of activity 401 can be combined or skipped.

In these or other embodiments, one or more of the activities of activity 401 can be implemented as one or more computing instructions configured to run at one or more processors and configured to be stored at one or more non-transitory computer-readable media. Such non-transitory computer-readable media can be part of a computer system such as prescription label scanner system 310 and/or web server 320. The processor(s) can be similar or identical to the processor(s) described above the respect to computer system 100 (FIG. 1).

Figure 11:
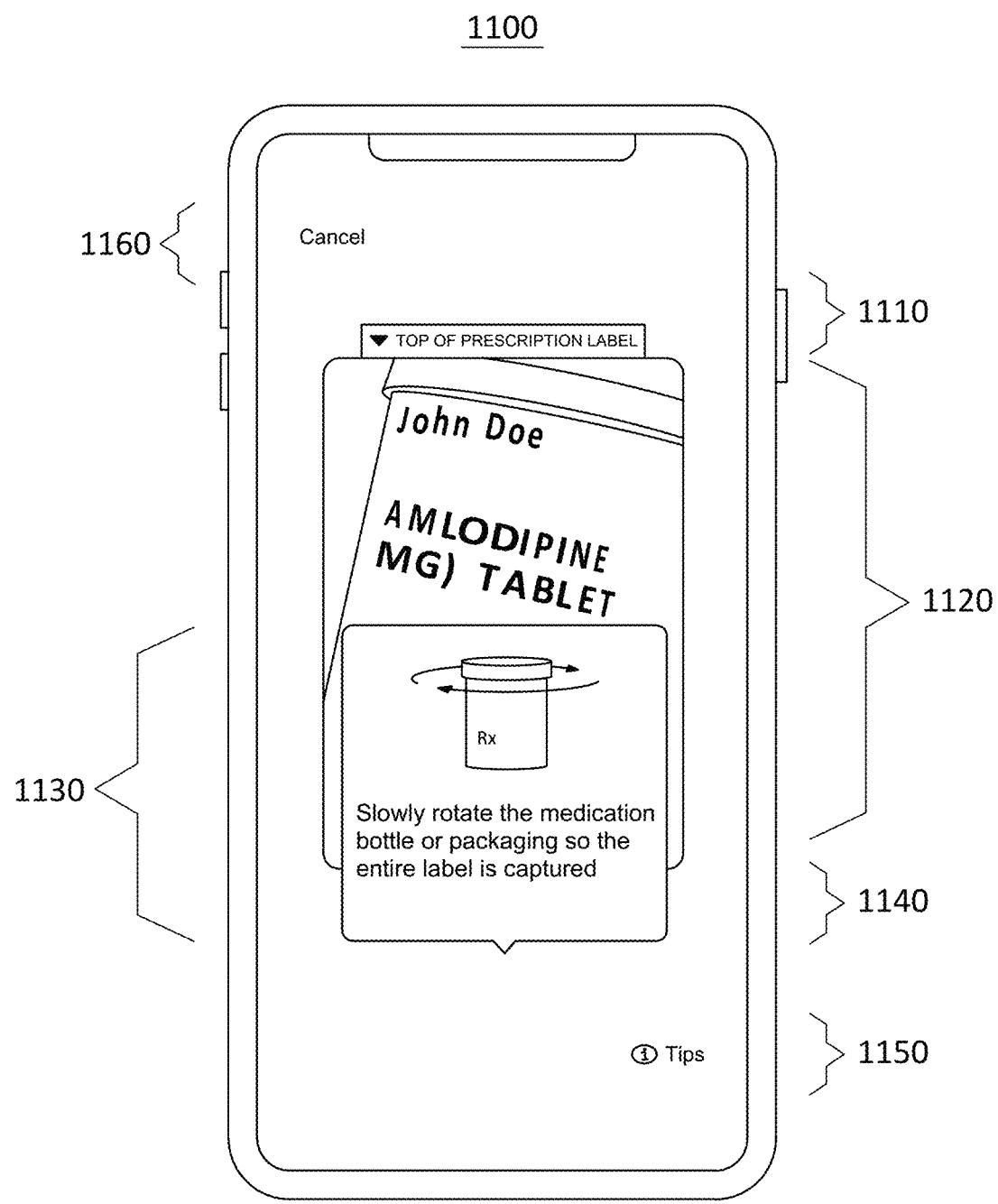
FIG. 11 illustrates an exemplary user interface display, according to an embodiment.

Referring to FIG. 5, activity 401 can include an activity 501 of, upon initiating the camera on the mobile device of the user, triggering a window interface to appear on the user interface of the mobile device. In several embodiments, the window interface can include a visual cue of where to point the camera lens to capture the area of interest using an overlay of an outline shape or a super imposed graphic of a boundary area, as described below in connection with exemplary user interface display 1100 (FIG. 11). In various embodiments, the area of interest for the camera lens can include a targeted portion of text or graphics on the object and/or medication package being videotaped. In some embodiments, the window interface outline or boundary area can be depicted and/or defined by a set of predetermined superimposed boundary lines (e.g., red lines or another colored set of lines) to define a set of outer edges and/or the periphery borders of the outline as displayed on the user interface. In several embodiments, window interface can be used as a visual guideline of where to place or position the prescription label or other intended area on the medication package in front of the camera lens to the user in real-time.

In various embodiments, the camera can automatically be activated (e.g., turned on) when one or more sensors within the mobile device detects the presence of an object (e.g., medication package) that has been placed in front of the camera lens. In some embodiments, the camera can be automatically activated when the sensors within the mobile device detect or sense that an object has been positioned within the set of boundary lines of the window interface displayed on the user interface of the mobile device. In some embodiments, in order to reduce inadvertent or unintended video images from being captured before the package is in an optimal position or placement, the camera can remain in an inactivated state (e.g., turned off) while the user searches for an optimal position or placement of the object in front of the camera lens. In various embodiments, the user can search for the optimal position by receiving instructions and/or recommendations, such instructions and/or recommendations can be similar or identical to activity 401 (FIG. 4).

Figure 10:
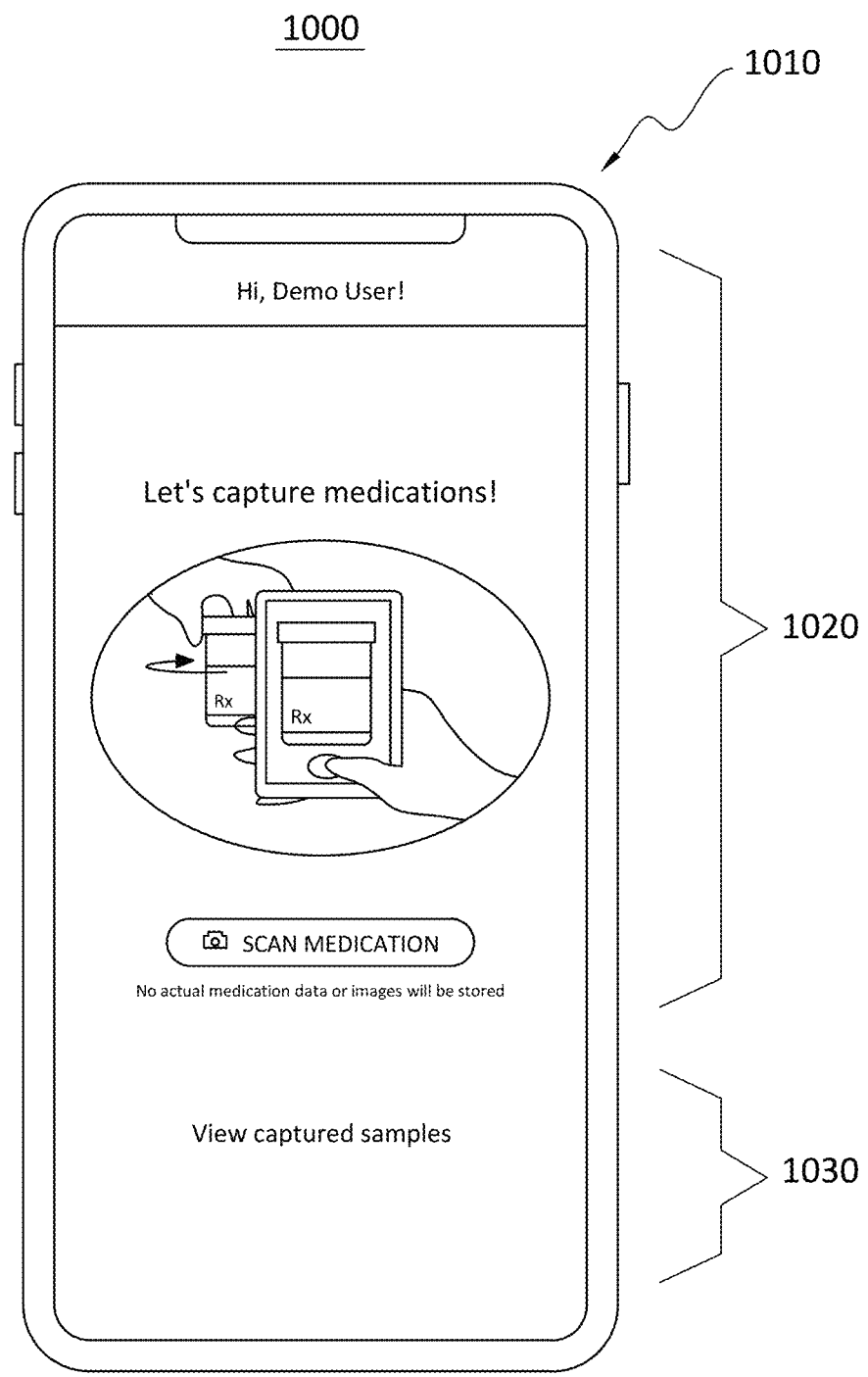
FIG. 10 illustrates an exemplary user interface display, according to an embodiment.

Jumping ahead in the drawings, FIG. 10 illustrates an exemplary user interface display 1000 showing an interactive screen display of a graphical user interface on a mobile device, according to another embodiment. User interface display 1000 is merely exemplary, and embodiments of a prescription label scanner for a medication package can be employed in many different embodiments or examples not specifically depicted or described herein. In a number of embodiments, user interface display 1000 can be an interactive webpage or software application (app) display to allow a user to capture a rotated view of a prescription label attached to a non-planar surface of a medication package. In some embodiments, user interface display 1000 can include a scan medication homepage display 1010, a scan medication selector 1020, and/or a stored medications selector 1030.

In several embodiments, scan medication home page display 1010 can be displayed as an interactive graphical user interface of a computing device and/or a user computer, such as user computer 340-341 (FIG. 3). In many embodiments, scan medication homepage 1010 can be used by a user, such as user 350-351 (FIG. 3), to initiate capturing a video of a rotated view of a non-planar surface of a medication package, such as a rounded medication bottle. In various embodiments, the medication package can include a planar surface, such as a flat bottle shape.

In some embodiments, scan medication selector 1020 can be selected to activate the camera. In many embodiments, the camera can be stationary while the medication package is rotated to scan or capture a video of the prescription label.

In several embodiments, medications selector 1030 can allow the user to view one or more saved prescriptions and/or medications from previous scans. In many embodiments, data from each video of the respective prescriptions can be stored in a database and/or on a cloud environment. In some embodiments, stored medications selector 1030 can allow the user to bypass initiating a new scan and jump directly to a list of historical medications stored. In several embodiments, a user and/or a caregiver can initiate a refill of a previous medication based on a refill date scanned from the prescription label. In various embodiments, the user and/or the caregiver can electronically transmit digital data associated with multiple mediations prescribed for the user to an authorized associate (e.g., pharmacist, health provider). In various embodiments, the user and/or the caregiver of the user also can automatically view a single medication of multiple medications and check for potential drug interactions prior to administering and/or taking the single medication. In some embodiments, the user and/or caregiver can transmit one or more prescriptions for medications prescribed to the user to an authorized entity (e.g., pharmacist, physician's office) to check for potential drug interactions across a list of current medications for the user.

Turning ahead in the drawings, FIG. 11 illustrates an exemplary user interface display 1100 showing an interactive screen display of a graphical user interface on a mobile device, according to another embodiment. User interface display 1100 is merely exemplary, and embodiments of prescription label scanner for a medication package can be employed in many different embodiments or examples not specifically depicted or described herein. In a number of embodiments, user interface display 1100 can be an interactive webpage or a software app display to allow a user to view and adjust a position, an angle, a perspective, and/or another suitable adjustment of the prescription label when viewed through the camera lens on the mobile device prior to generating the video of the rotated view of the label.

In some embodiments, user interface display 1100 can include a window interface display 1110, an outline interface display 1120, an instruction interface display 1130, an selector 1140, a tip request selector 1150, and/or a cancel feature selector 1160.

In several embodiments, window interface display 1110 can allow the user to point the camera lens at the targeted prescription label and receive a prompt or a feedback direction showing the user how to align the prescription label with the camera lens. In some embodiments, window interface display 1110 can act as an automatic user interface assist feature that automatically guides the user before turning on the camera. For example, when the user points the camera lens over the label, a prompt at the top of a window interface display can indicate where the top of the prescription label should line up. Such a prompt can include a text box with instructions and/or an arrow associated with the text box allowing the user to align the top of the label below the arrow.

In many embodiments, outline interface display 1120 can include a boundary outline displayed as part of the window interface display. In some embodiments, outline interface display 1120 can be an overlay window display and/or another suitable outline display. In several embodiments, outline interface display 1120 can be automatically triggered upon activation of the camera on the mobile device. In several embodiments, triggering an outline interface display 1120 can include selecting a button or icon (not shown) when the user is ready to begin capturing the video and ready to begin rotating the medication package aligned within the boundary outline on the window interface display.

In various embodiments, instruction interface display 1130 can include a pop-up box or a pop-up text box with particular step by step instructions for the user to follow in real-time as the user rotates the medication package in front of the camera on the mobile phone. Such instructions can include directions to the user, such as, "Slowly rotate the medication bottle or packaging so the entire label is captured."

In many embodiments, selector 1140 can allow the user to indicate that the label has been aligned with the instructions from the pop-up box and the process can proceed. In several embodiments, the feature can be interactive text such as "got it" that appears as part of instruction interface display 1130.

In some embodiments, a tip request selector 1150, can allow the user to manually request a display of tips (e.g., suggestions) and/or auto-capture tips associated with capturing the video of the medication package. In many embodiments, selecting tip request selector 1150 can include automatically detecting the presence of a prescription label within the boundary lines of outline interface display 1120, which detection data can prompt the system to retrieve and display one or more tips (e.g., auto-capture tips) relevant to viewing the prescription label within the outline interface display 1120.

In several embodiments, a cancel feature selector 1160 can allow the user to stop and/or cancel the video process at a point in time. In some embodiments, cancel feature selector 1160 also can allow the user to re-start the scanning process at a point in time as a new video. In several embodiments, cancel feature selector 1160 can allow the user to pause the video process at a point in time and/or to continue scanning the prescription label once the label is realigned with the previous image of an incomplete video.

Turning ahead in the drawings, FIG. 12 illustrates an exemplary user interface display 1200 showing an interactive screen display of a graphical user interface on a mobile device, according to another embodiment. In many embodiments, user interface display 1200 is merely exemplary, and embodiments of prescription label scanner for a medication package can be employed in many different embodiments or examples not specifically depicted or described herein. In a number of embodiments, user interface display 1200 can be an interactive webpage or a software app display to allow a user to view a particular image of a portion of prescription label and view one or more auto-capture tips associated with the particular image.

In some embodiments, user interface display 1200 can include auto-capture tips display 1210 and/or an image interface display 1220.

In several embodiments, auto-capture tips display 1210 can display particular auto-capture tips during the video process for corrective action. In various embodiments, auto-capture tips display 1210 can include a help mode and/or a request mode that can be displayed prior to the video process. In some embodiments, the help mode and/or the request mode can be displayed during the action of capturing the video of the prescription label simultaneously as the medication package is rotated. For example, the auto-capture tips can include such instructions as "rotate the medication bottle slowly and ensure all of the label's content remains inside the frame", or "grip the edges of the medication in order to capture as much of the label information possible" or "hold phone steady and make sure there is good lighting," and/or another suitable auto-capture tip.

In a number of embodiments, image interface display 1220 can show the user an image as viewed by the camera lens associated with one or more auto-capture tips, such auto capture tips can pertain to modifying and/or adjusting the medication package aligned with the camera lens.

Turning back to FIG. 5, in a number of embodiments, activity 401 can include an activity 502 of, upon sensing that the camera is pointed at the medication package and that the medication package is viewed within the boundary lines of the outline of the window interface, automatically triggering an image box comprising one or more instructions to rotate the medication package while capturing the video of the rotated view of the medication package within the window interface. In some embodiments, the one or more instructions can include auto-capture tips. In some embodiments, the auto-capture tips can include instructions prompting and/or assisting the user to perform an adjustment for the camera lens, the camera position, the position or the view of the medication package, and/or another suitable instruction to capture the video images, as described above in connection with exemplary user interface 1200 (FIG. 12). In many embodiments, the camera on the mobile device can remain in a substantially stationary position while the medication package is rotated in front of the camera lens.

In various embodiments, activity 502 also can include providing a user interface assist feature that can sense and/or detect when a medication package is beyond the scope of the boundary lines of the window interface outline for the camera lens. In many embodiments, the user interface assist feature can be opened and/or triggered to open as another window (e.g., pop up box) displayed and/or overlaid on the window interface displaying a set of instructions and/or recommendations. In several embodiments, the set of instructions can include instructions to adjust a position of a medication package while being viewed by the window interface. In some embodiments, sensing the placement of the medication package can include one or more sensors working in concert with the camera in the user device, a computing device, and/or another suitable device. In many embodiments, triggering a window interface can begin with determining and/or sensing that the target medication package is within the outer boundary lines of the window interface. In various embodiments, that window interface can sense when the target medication package is not aligned within the outer boundary lines. For example, such instructions to adjust the positioning of the medication package can include "line the edges of the prescription information with the red lines and tap to continue" and/or "for best image quality: ensure there is good lighting or hold the camera steady," and/or another suitable corrective instruction to re-position the medication package prior to initiating the camera to begin capturing the video image. In many embodiments, the system can be programmed to include an automatic feature that sends out an audible sound when the medication package is not aligned to capture the label and/or an automated pause feature that prevents the camera from turning on until the medication package is aligned within the outer boundary lines.

Figure 13:
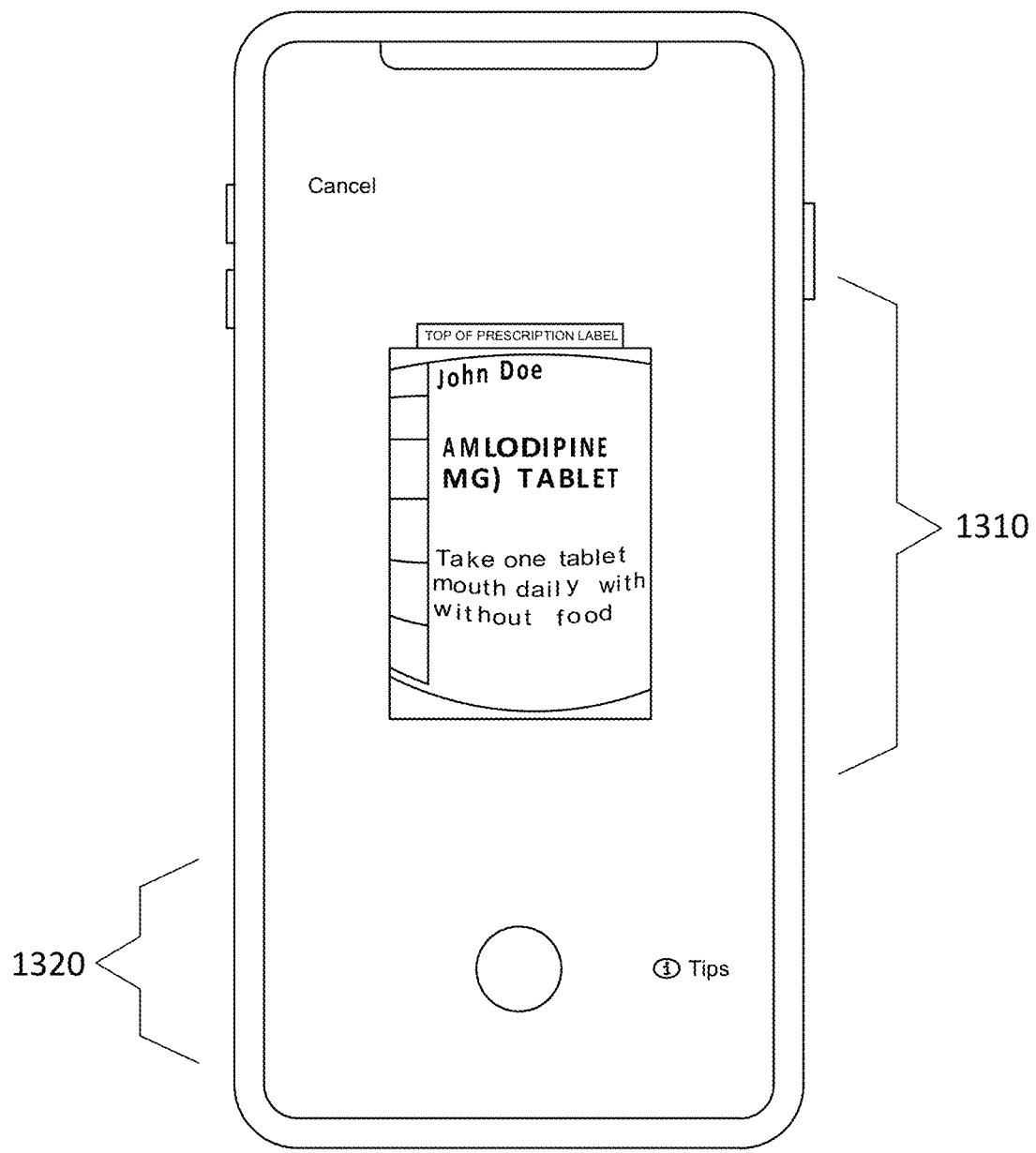
FIG. 13 illustrates an exemplary user interface display, according to an embodiment.

Jumping ahead in the drawings, FIG. 13 illustrates an exemplary user interface display 1300 showing an interactive screen display of a graphical user interface on a mobile device, according to another embodiment. User interface display 1300 is merely exemplary, and embodiments of prescription label scanner for a medication package can be employed in many different embodiments or examples not specifically depicted or described herein. In a number of embodiments, user interface display 1300 can be an interactive webpage or a software app display to allow a user to begin scanning a video of the prescription label by initiating the camera on the mobile device.

In some embodiments, user interface display 1300 can include scan interface display 1310 and/or a camera button 1320.

In several embodiments, scan interface display 1310 can allow the user to view in real-time the portion of the prescription label concurrently as the camera is capturing the video images and while the user is rotating the medication package.

In some embodiments, camera button 1320 can allow the user to start or initiate the camera to begin capturing the video images by selecting or depressing camera button 1320. Camera button 1320 also can be an icon, located on another area of a user interface, a speaker icon for a voice-activated technique, and/or another suitable technique to initiate a camera on a mobile device.

Returning back in the drawings to FIG. 4, method 400 also can include an activity 402 of capturing, using the camera, the video of the rotated view of the non-planar surface of the medication package. In various embodiments, rotating the medication package can include rotating the medication package or a non-planar object 360 degrees (e.g., a full circle view) or a portion thereof to capture the text data and/or images (e.g., bar codes, logos) on the label attached to the medication package, based on instructions provided, as described above in connection with activities 501-502 (FIG. 5), and as shown in user interface displays 1000 (FIG. 10), 1100 (FIG. 11), and/or 1200 (FIG. 12), all as described above.

In many embodiments, rotating the medication package can include keeping the camera stationary at an approximately fixed distance from the medication package while the medication package is rotated. In several embodiments, an optimal fixed distance from the medication package can be detected or sensed using sensors in the camera. In some embodiments, the fixed distance can be displayed as an alert displayed on the window interface.

In several embodiments, method 400 additionally can include an activity 403 of generating, using an input pre-processing algorithm, a series of images from the video. In some embodiments, each of the images in the series of images can show a respective portion of the non-planar surface. In many embodiments, the series of images captured from the video can undergo one or more pre-processing approaches and/or techniques to prepare and/or adjust each image into a legible format and/or a machine readable format. In several embodiments, an optical character recognition (OCR) technique can read the legible format and/or machine readable format for each character of the text and/or an image as preprocessed. For example, a character of text and/or an image can be blurred or warped in such a way that the OCR techniques implemented can incorrectly identify a character or can incorrectly misidentify a character or can skip over the character by not recognizing a character as text within a label. As another example, an incorrectly identified character can change a meaning or definition of a prescription medication, an instruction on how to administer the medication, an expiration date, a refill date, no refill restriction, a warning not to combine a medication with another medication and/or food and/or another suitable meaning in a prescription label.

Turning back to the drawings in FIG. 4, activity 403 also can include identifying (e.g., detecting) one or more issues for correction within each image, such issues can include an image anomaly, an image distortion, an illegible image, an illegible character of an image, and/or another suitable image issue that is associated with a lower quality (e.g., unclear) copy compared to the original image. Activity 403 also can include various algorithms, technological processes, and/or technological approaches that can be implemented to enhance, correct, and/or modify portions of the images that produce the lower quality image. In many embodiments, activity 403 can include various types of pre-processing, as shown in FIG. 6 and described below.

Figure 14:
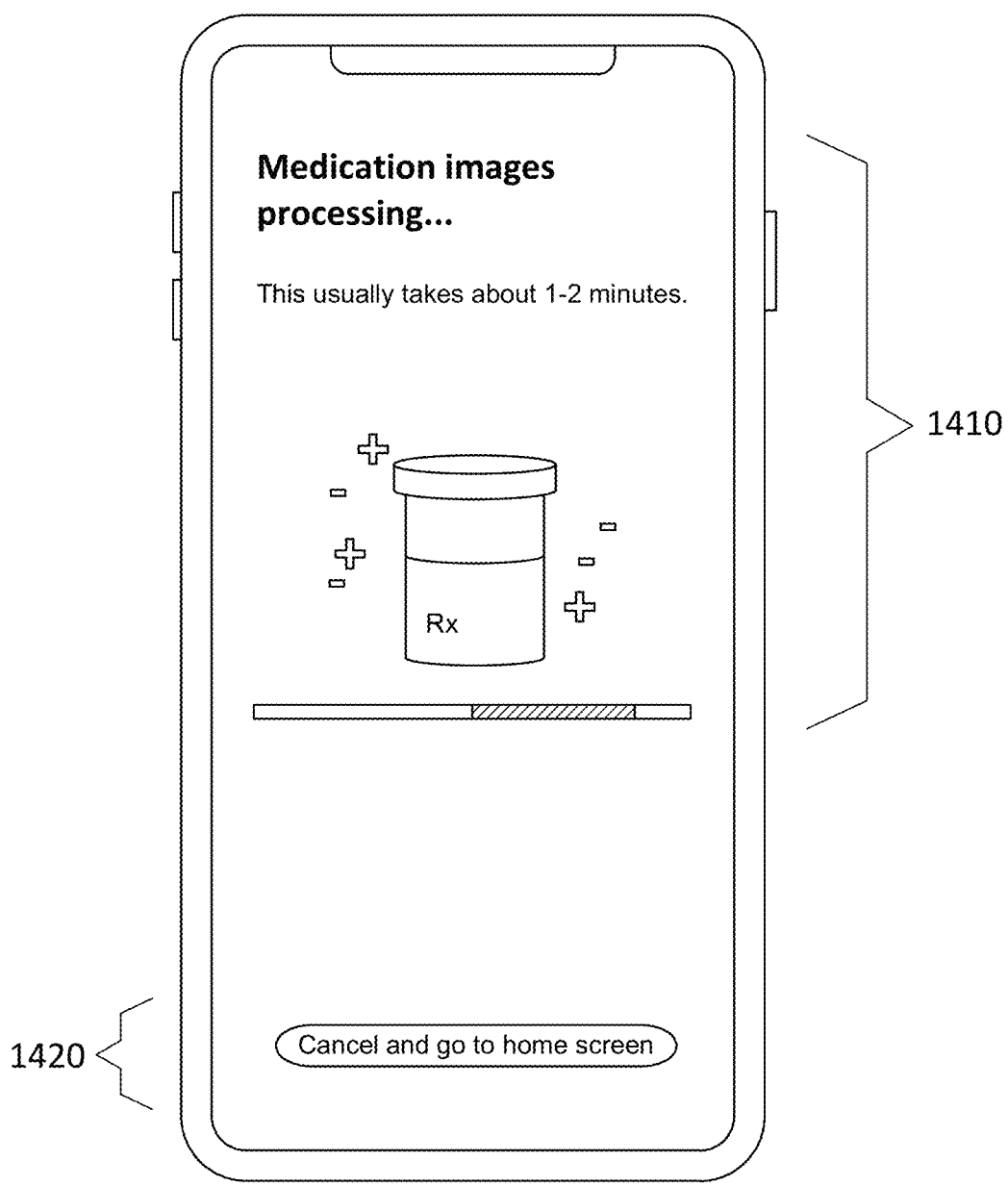
FIG. 14 illustrates an exemplary user interface display, according to an embodiment.

Jumping ahead to the drawings, FIG. 14 illustrates an exemplary user interface display 1400 showing an interactive screen display of a graphical user interface on a mobile device, according to another embodiment. User interface display 1400 is merely exemplary, and embodiments of prescription label scanner for a medication package can be employed in many different embodiments or examples not specifically depicted or described herein. In a number of embodiments, user interface display 1400 can be an interactive webpage or a software app display to allow a user to initiate pre-processing of each of the images of the video captured by the camera.

In some embodiments, user interface display 1400 can include an image processing display 1410 and/or a cancel image selector 1420.

In several embodiments, image processing display 1410 can display a progress of processing of the series of images captured from the video using one or more of input pre-processing algorithms and/or another suitable input pre-processing approach. Such input pre-processing algorithms can be similar or identical to activities 601 through 610, as shown in FIG. 6 and described below. For example, image processing display 1410 can be activated to show the progress of processing one or more selected video images to clarify the image (e.g., a blurred image), correct a visual defect (e.g., illegible fonts), modify the perspective of the image, and/or another suitable irregularity associated with image processing. In many embodiments, image processing display 1410 can display the actions associated with one or more input pre-processing algorithms and/or techniques. In various embodiments, image processing display 1410 can display a time period indicating the amount of time remaining to process images using the one or more input pre-processing algorithms and/or techniques.

In some embodiments, cancel image selector 1420 can allow the user to cancel the actions and/or any of the one or more input pre-processing algorithms and/or techniques either prior to and/or during the actions associated with the one or more input pre-processing algorithms and/or techniques. In several embodiments, after the completion of the actions associated with the one or more input pre-processing algorithms and/or techniques, cancel image selector 1420 can allow the user to return (e.g., go back) to a home screen, another web page screen, and/or another suitable screen displayed on the user interface.

Jumping ahead in the drawings, FIG. 6 illustrates a flow chart for activity 403 of generating, using an input pre-processing algorithm, a series of images from the video, wherein each of the images shows a respective portion of the non-planar surface, according to an embodiment. Activity 403 is merely exemplary and is not limited to the embodiments presented herein. Activity 403 can be employed in many different embodiments and/or examples not specifically depicted or described herein. In some embodiments, the procedures, the processes, and/or the activities of activity 403 can be performed in the order presented. In other embodiments, the procedures, the processes, and/or the activities of activity 403 can be performed in any suitable order. In still other embodiments, one or more of the procedures, the processes, and/or the activities of activity 403 can be combined or skipped.

In these or other embodiments, one or more of the activities of activity 403 can be implemented as one or more computing instructions configured to run at one or more processors and configured to be stored at one or more non-transitory computer-readable media. Such non-transitory computer-readable media can be part of a computer system such as prescription label scanner system 310 and/or web server 320. The processor(s) can be similar or identical to the processor(s) described above the respect to computer system 100 (FIG. 1).

In some embodiments, activity 403 can include an activity 601 of mapping light and dark areas, using image inversion, to create a digital negative of an image of the video. In several embodiments, input pre-processing of an image can include using image inversion to automatically adjust and/or sharpen a contrast between the light and dark areas of the image to generate a positive image. For example, adjusting the contrast of the digital negative can be conducted using a reversed image or a mirror image of the image across a horizontal axis to compose (e.g., form) each of the elements or characters of each image. Such an image inversion process can illustrate a technique based on mapping light and dark areas of an image to create a black and white digital negative of a particular view and/or portion of a prescription label as described in greater detail above in connection activity 601.

In several embodiments, activity 403 also can include an activity 602 of adding, using dilation image processing, one or more first pixels to outer borders of elements of the image. For example, the number of pixels added to the outer borders of the image can be used to enlarge the image based on a particular shape of the image.

In some embodiments, activity 403 further can include an activity 603 of removing, using erosion image processing, one or more second pixels from the outer borders of the elements of the image. For example, removing a number of pixels from the borders of the image can depend on the number of thin lines or image islands detected on the image of the video to preserve the shape and size of the object in the image, such as a rounded medication package.

Figure 19:
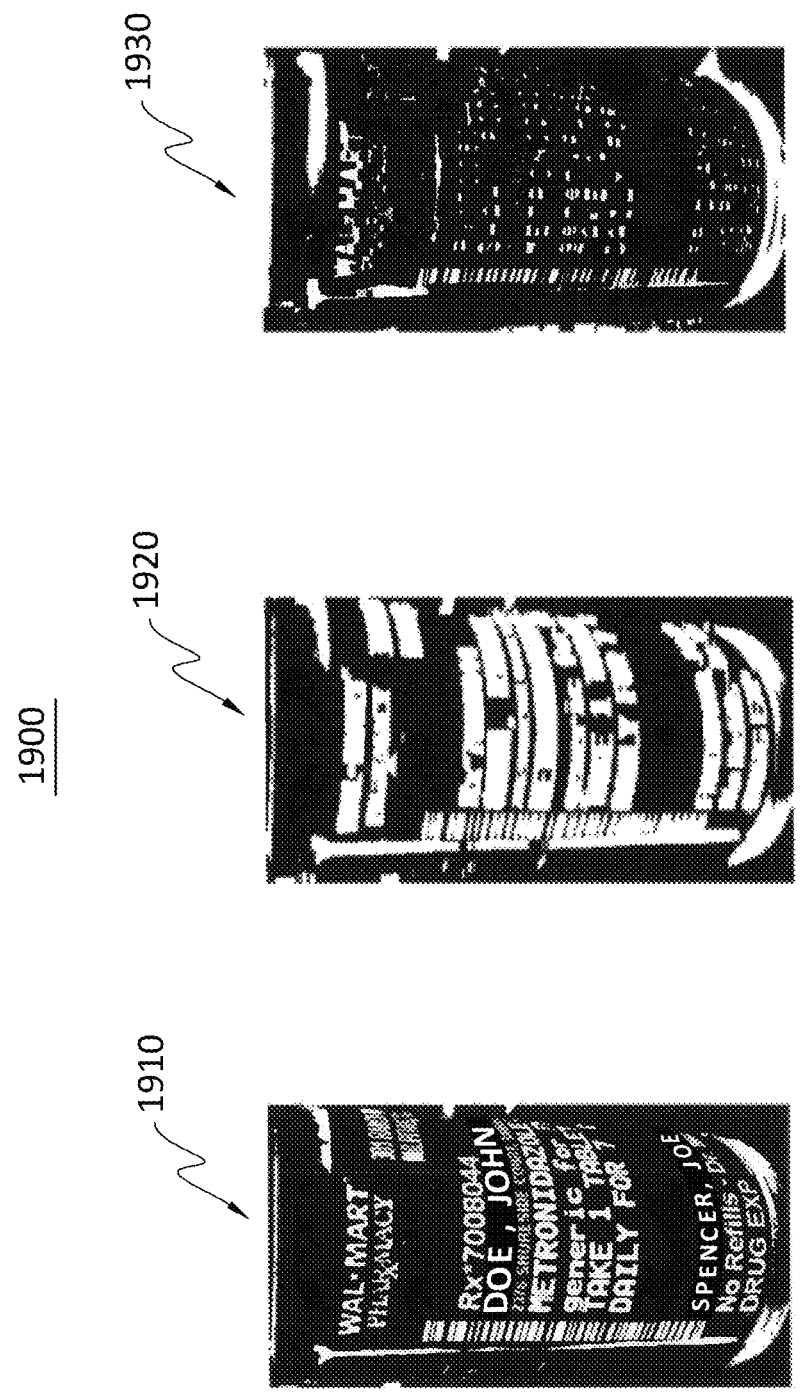
FIG. 19 illustrates a set of images used and/or created in image pre-processing techniques, such as image inversion, dilation image processing, and erosion image processing.

Jumping ahead in the drawings, FIG. 19 illustrates a set of images 1900 used and/or created in image pre-processing techniques, such as image inversion, dilation image processing, and erosion image processing. Set of images 1900 shows exemplary outputs of activities 601 thru 603 (FIG. 6). Set of images 1900 includes an image 1910 illustrating image inversion, an image 1920 illustrating dilation image processing, and an image 1930 illustrating erosion image processing.

Image 1910 illustrates an exemplary output image created using image inversion, displayed as a digital negative of a pre-processed original image (e.g., frame of a video) that can be used to create a clearer or legible text and/or images. Such image inversion approaches can be similar or identical to using image inversion approaches and/or techniques of activity 601 (FIG. 6). For example, an image selected from a video displaying a portion of a prescription label attached to a rounded surface often can have particular areas of text and/or images that appear illegible or not clear enough to be read.

Image 1920 illustrates an exemplary output image created using dilation image processing, showing a visual effect (e.g., pixel definition) that can occur by adding pixels to the area of interest to increase a portion of a region or area of an image. Image 1930 illustrates an exemplary output image created using erosion image processing, showing a visual effect (e.g., pixel definition) that can occur by removing pixels to the area of interest to decrease a portion of a region or area of an image. In general, dilation and erosion image processing techniques are often used in combination together as morphological operations for digital images.

Returning in the drawings to FIG. 6, in a number of embodiments, activity 403 also can include an activity 604 of modifying, using image rescaling, a size of the image to a different scale.

Such a process can normalize pixel values of a predetermined range between zero and one, where a value of zero can indicate to not re-size the letter or character. For example, the rescaling image processing technique can be used to rescale a predetermined height of each capital letter in the text of an image, such as a height between 20 and 30 pixels.

Returning to FIG. 6, activity 403 further can include an activity 605 of assigning a thresholding value to one or more pixels of the image to contrast a background area of the image from a foreground area of the image. Thresholding can be performed to isolate objects in a digital image of the video by replacing each pixel in an image with: (i) a black pixel when the image intensity is less than a fixed constant or (ii) a white pixel when the image intensity is greater than the fixed constant.

Figure 20:
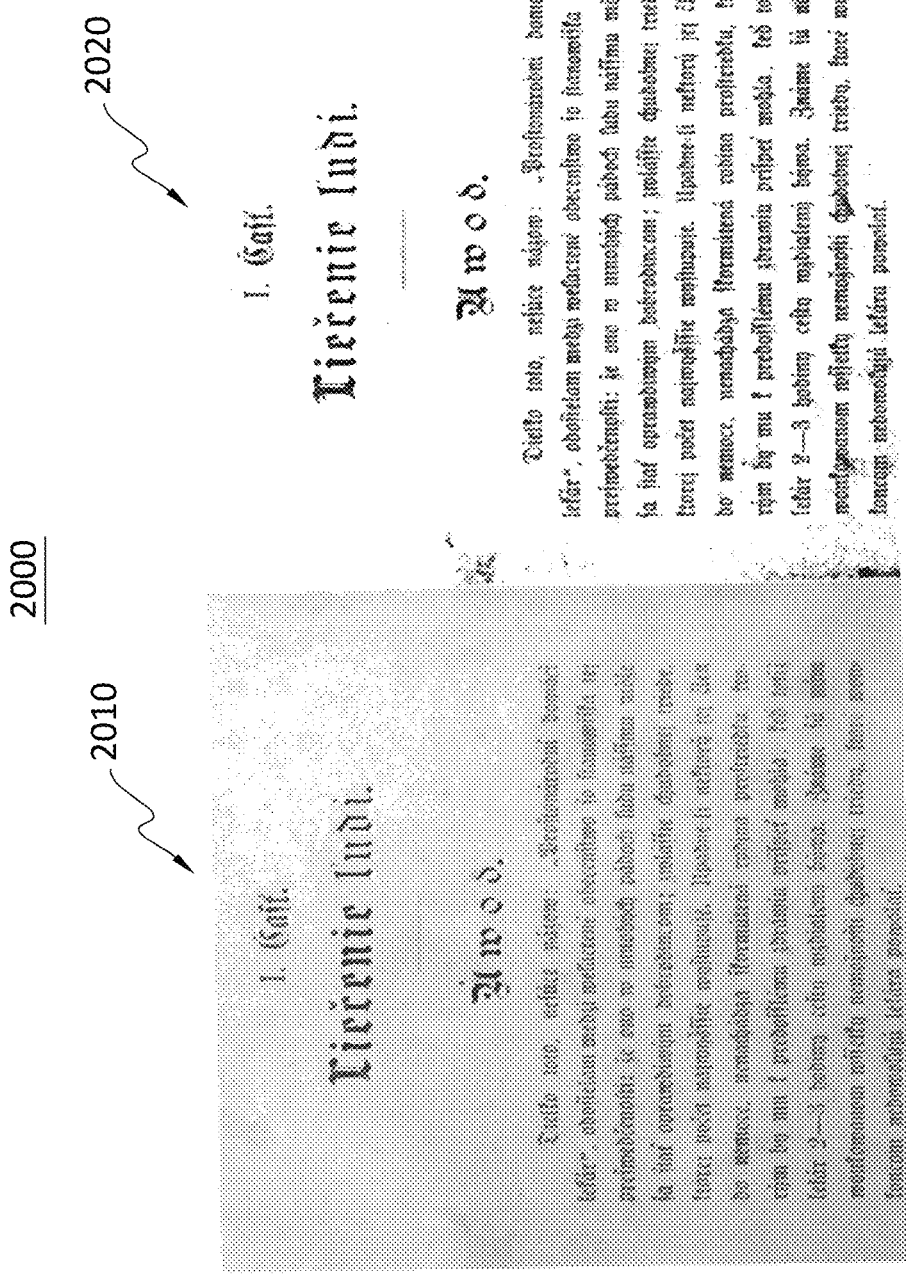
FIG. 20 illustrates a set of images used and/or created in image pre-processing techniques, such as binarization and thresholding.

In many embodiments, activity 403 additionally can include an activity 606 of partitioning the image using image binarization processing to detect gray scale values of the images. Binarization can include converting a gray scale image into a binary image of black and white pixels. Binarization techniques can be used to distinguish the text and the background pixel values of the image. Binarization can often be combined with thresholding the image by setting white and black pixel values based on a thresholding value, which can be similar or identical to thresholding values used in activity 605. Jumping ahead in the drawings, FIG. 20 illustrates a set of images 2000 used and/or created in image pre-processing techniques, such as binarization and thresholding. Set of images 2000 shows exemplary outputs of activity 605 (FIG. 6) and activity 606 (FIG. 6). Set of images 2000 includes an image 2010 illustrating image binarization and an image 2020 illustrating thresholding.

Image 2010 illustrates image binarization by converting the image into a gray scale image by assigning white pixel values and black pixel values in the gay scale image based on a thresholding value. Image 2020 illustrates thresholding, showing the effects of isolating objects in a digital image of the video by replacing each pixel in an image with a black pixel or a white pixel based on the image intensity of the image.

Turning back to FIG. 6, activity 403 further can include an activity 607 of defining borders of the image.

Figure 21:
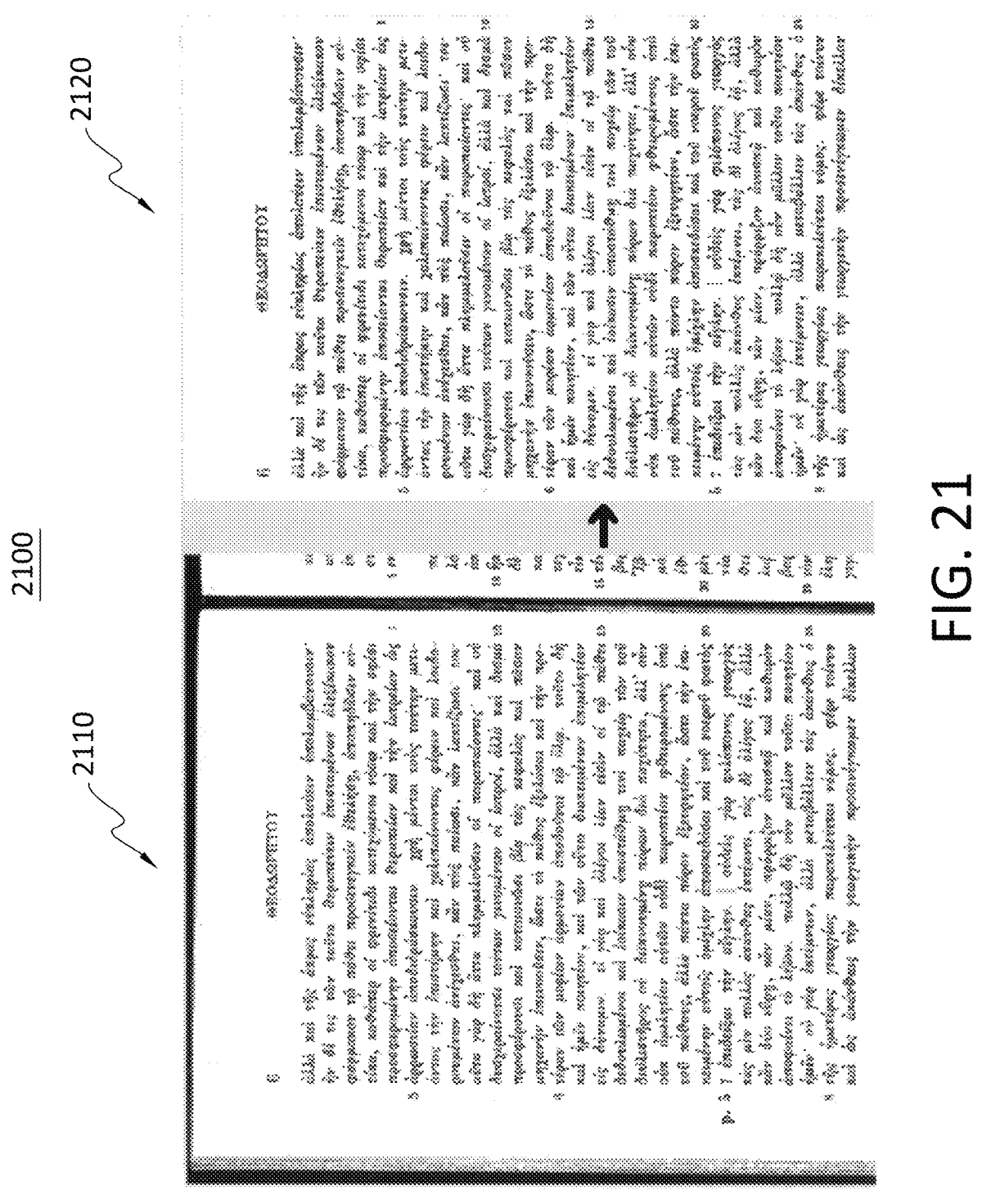

Jumping ahead in the drawings, FIG. 21 illustrates a set of images 2100 used and/or created in image pre-processing techniques, such as defining borders. Set of images 2100 shows exemplary outputs of activity 607 (FIG. 6). Set of images 2100 includes image 2110 and image 2120.

Image 2110 illustrates an unprocessed image with undefined borders of a page in a book. Image 2120 illustrates the output of a process of defining the border of the unprocessed image into a processed image of the page in the book with equal border areas of the page surrounding the text.

Turning back to FIG. 6, activity 403 also can include an activity 608 of rotating the image. In some embodiments, activity 608 of rotating the image can be performed before activities 609 and/or 610, described below.

In several embodiments, activity 403 additionally can include an activity 609 of deskewing the image to align the image horizontally and vertically. In various embodiments, deskewing the image can be a process of straightening a scanned image where the image slants in one direction or is misaligned on the page.

Figure 22:
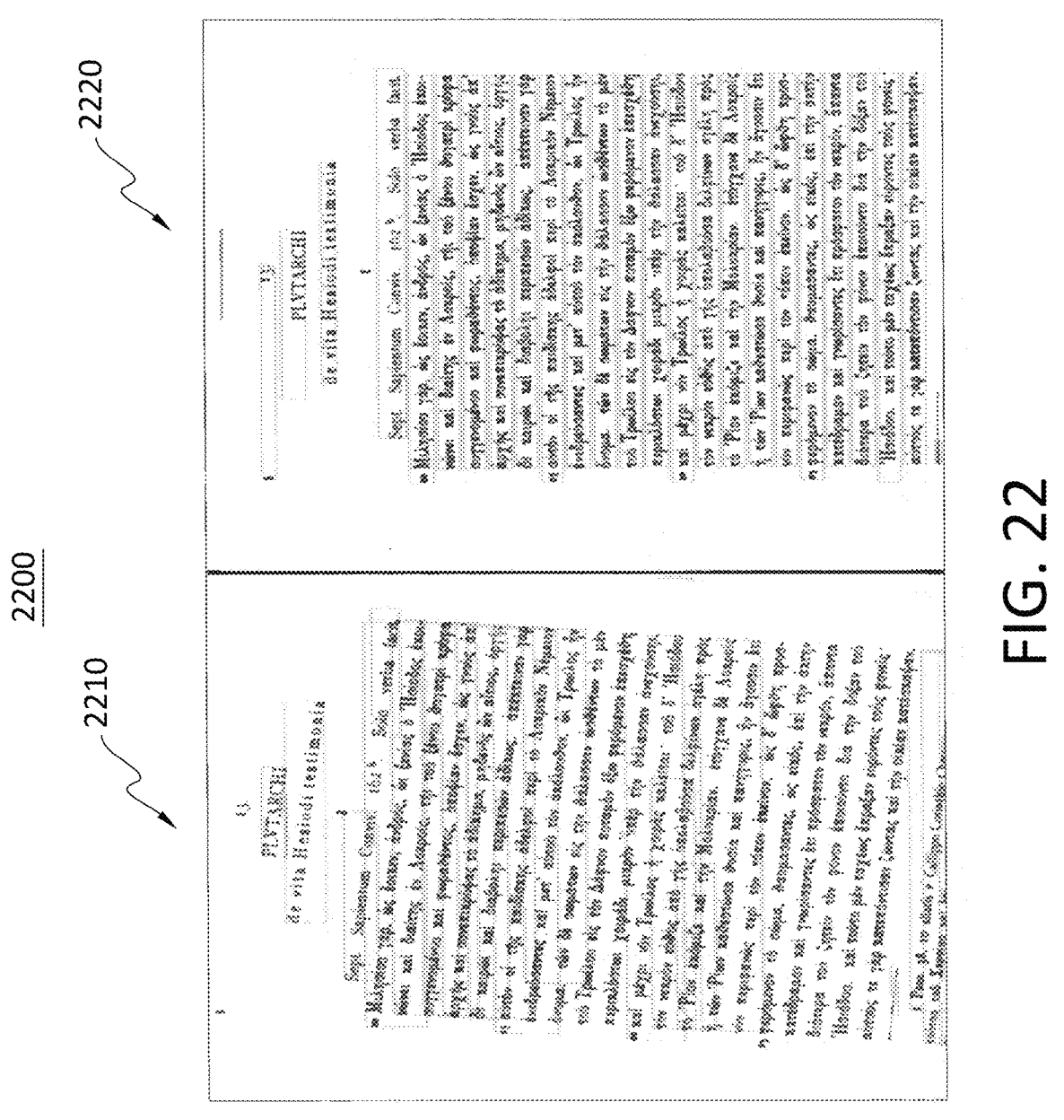

Jumping ahead to the drawings, FIG. 22 illustrates a set of images 2200 used and/or created in image processing techniques, such as deskewing. Set of images 2200 shows exemplary outputs of activity 608 (FIG. 6) and activity 609 (FIG. 6). Set of images 2200 includes image 2210 and image 2220.

Image 2210 illustrates an unprocessed image of a text on a page in a book where the text in the image of the page is not aligned horizontally or vertically on the image. For example, superimposing text boxes for each sentence or phrase on the page shows that the text is not aligned horizontally in a straight line. Image 2220 illustrates a page that has been deskewed showing that the text has been straightened out horizontally as indicated by the superimposed text boxes on the page.

Returning to FIG. 6, activity 403 also can include an activity 610 of de-warping the image to remove warp distortion of the image. De-warping can refer to a process of correcting a perspective of an image or to reverse geometric distortions caused by a camera lens when the horizontal and vertical lines of the image are curved. De-warping techniques can include a process of digitally manipulating the image by calibrating the disparity on the horizontal and vertical lines and transforming the camera image to be straight and perpendicular.

In several embodiments, one or more of activities 601-610 can be one or more intermediate processes used in generating a series of images from the video of activity 403, where the output from each of activities 601-610 can be received as an input to another one of activities 601-610.

Figure 23:
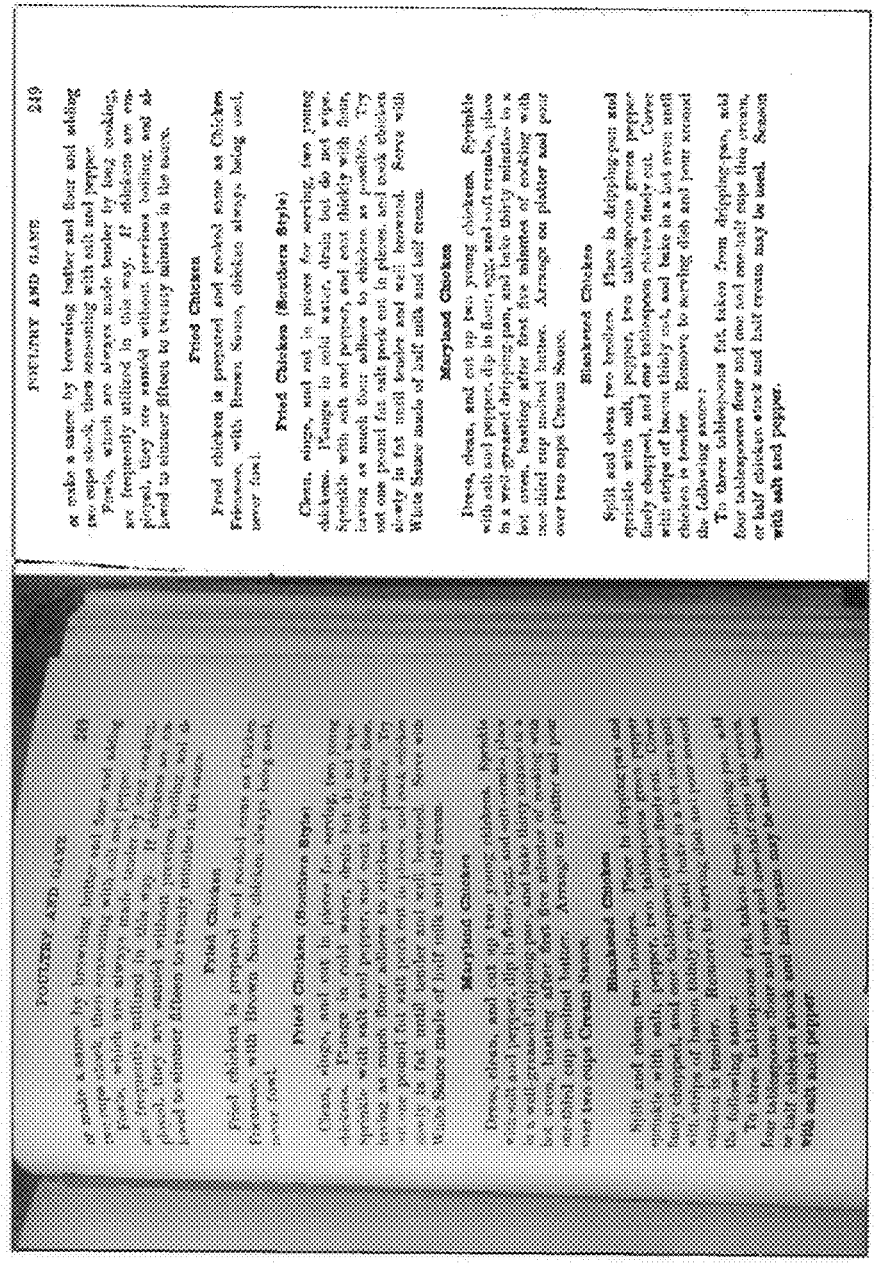
FIG. 23 illustrates a set of images used and/or created in image pre-processing techniques, such as dewarping.

Jumping ahead to the drawings, FIG. 23 illustrates a set of images 2300 used and/or created in image pre-processing techniques, such as dewarping. Set of images 2300 shows exemplary outputs of activity 610 (FIG. 6). Set of images 2300 includes image 2310 and image 2320.

Image 2310 illustrates a geometric distortion of the image of a page of a book caused by the camera lens. Image 2320 illustrates the process of de-warping the curved lines in de-warping image 2310 into straight and perpendicular lines of the text on the page.

Returning back to FIG. 4, method 400 further can include an activity 404 of converting respective segments of text in the respective portion of the non-planar surface within each of the images into respective machine-readable text data using an optical character recognition (OCR) algorithm. In many embodiments, an advantage of converting each of the images into respective machine-readable text data can include reading each pre-processed character of the image previously pre-processed using the input pre-processing algorithm to increase the reliability and accuracy of using the OCR algorithm. In several embodiments, OCR algorithms and/or techniques can include Google Vision Application Programing Interface (API), Microsoft Vision API, Tesseract API, or another suitable OCR API.

In many embodiments, method 400 also can include an activity 405 of recognizing, using an output post-processing algorithm, one or more respective words from the respective machine-readable text data corresponding to the respective segments of text in the respective portion of the non-planar surface within each of the images. In various embodiments, activity 405 can include multiple segmentation approaches implemented on the respective machine-readable text data. In some embodiments, the output post-processing algorithm can be optimized or programmed to recognize words and sentences using the machine-readable text output by the OCR algorithm. In several embodiments, a segmentation approach or technique can include an OCR default segmentation approach, such as a Tesseract OCR default segmentation.

In some embodiments, activity 405 also can include segmenting the machine-readable text data to recognize the one or more respective words based at least in part on customized receipt codes. In various embodiments, a segmentation approach or technique can include a custom segmentation approach that can be programmed to recognize other text data processed using an OCR algorithm such as text data found on a receipt, codes, and other text formats customized to recognize an applicable segmentation consistent with another text format.

In several embodiments, activity 405 further can include segmenting the machine-readable text data to recognize the one or more respective words based at least in part on one or more customized medical dictionaries. In many embodiments, the custom segmentation approach can include adding a customized vocabulary and/or medical terminology obtained from the one or more customized medical dictionaries to allow the output post-processing algorithm to recognize medical words and medical sentences associated with a prescription from the respective machine-readable text data corresponding to the respective segments of text. In some embodiments, the custom segmentation approach can include disabling particular dictionaries to increase the recognition abilities of the output post-processing algorithm when a majority of the text data is not associated with the particular dictionaries. In various embodiments, adding the customized medical dictionaries and/or disabling other particular dictionaries can be performed independently of each other and/or simultaneously. In many embodiments, adding the customized medical dictionaries and/or disabling other particular dictionaries can be performed in any order or sequence at any time.

Figure 7:
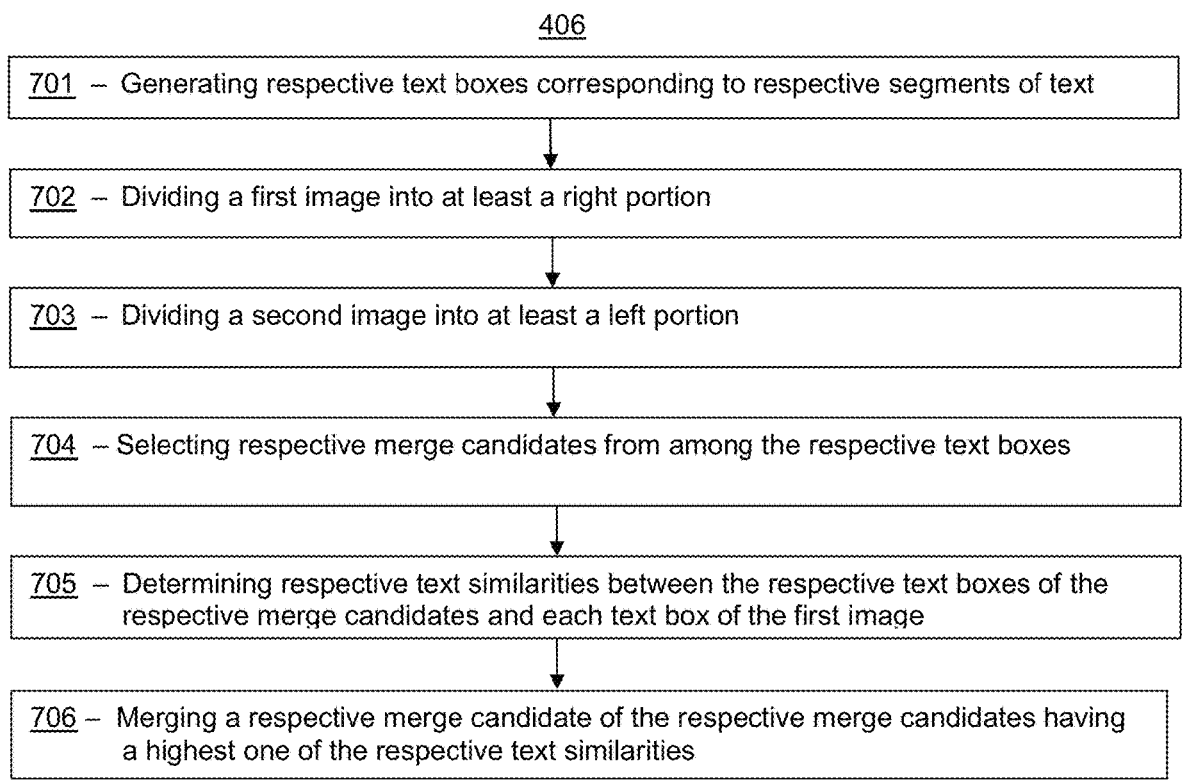
FIG. 7 shows an embodiment of activity of FIG. 4 of merging, using a merging algorithm, the one or more respective words from the images to create lines of text.

In various embodiments, method 400 additionally can include an activity 406 of merging, using a merging algorithm, the one or more respective words from the images to create lines of text. The merging algorithm can be the longest common substring algorithm described below, or another suitable algorithm.+ In many embodiments, the merging algorithm can analyze an output of a word received from the output post-processing algorithm representing one particular portion of the prescription label and analyze another output of the same word from another adjacent portion of the prescription label where each portion of the word can include part of the same letters or an overlap of letters of the same word. For example, portion A can include a first part of a word fragment and portion B can include a second part of the word fragment with one or more letters overlapping each word fragment. By using the merging algorithm, portion A and portion B of the same word can compose the whole word by merging the common letters of the word to generate the word then additional words to generate a line of text, as described below in connection with activities 701-706 (FIG. 7). In a number of embodiments, activity 406 can include merging a respective longest common substring of the respective merge candidate with the longest common substring of the each text box to a respective line of text across the first image and the second image.

Figure 24:
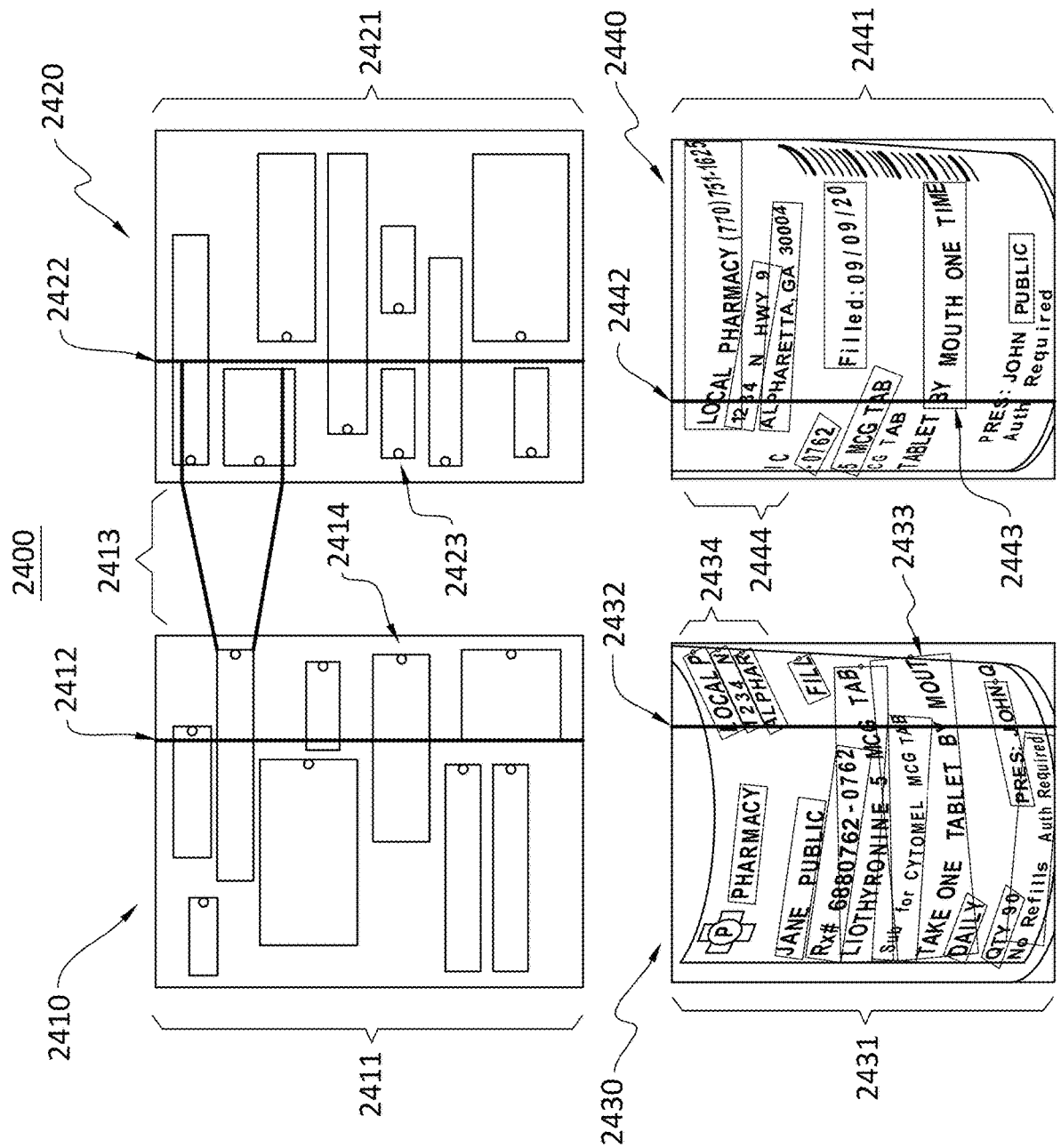
FIG. 24 illustrates a set of images used and/or created in merging text from two images.

Jumping ahead in the drawings, FIG. 24 illustrates sets of images 2400 used and/or created in merging text from two images, such as performing activity 406 (FIG. 4).

Sets of images 2400 include two exemplary sets of images of the prescription label displayed in two different formats: (i) outline images (e.g. outline images 2410 and 2420), which can in a box format without text, and (ii) a text label images (e.g., text label images 2430 and 2440), which can be with text. Each of the outline images (e.g., 2410, 2420) are positioned above a text label image (e.g., 2430, 2440). Each outline image (e.g., 2410) without text corresponds to the text label image below it. For example, outline image 2410 is a line-drawing of text label image 2430 and located above text label image 2430. Similarly, outline image 2420 is a line-drawing of text label image 2440 and located above text label image 2440.

Sets of images 2400 shows an example of how to merge two or more images (e.g., frames of the video) of a prescription label by matching text boxes with similar content mapped from one image to the other image, which process can be similar or identical to activities 701-704 (FIG. 7), described below. In FIG. 24, text label 2430 is placed side-by-side next to text label 2440, creating a left image and a right image of the label. It can be determined which of the text boxes from the left image and the right image can be considered as merge candidates. Both text label 2430 and text label 2440 further show how to generate respective text boxes corresponding to respective segment of text, similar or identical to activity 701 (FIG. 7), described below.

Outline image 2410 illustrates another version of the left image of text label image 2430 without the addition of text and/or images. Outline image 2410 presents a set of line drawings (e.g., empty boxes) corresponding to the text boxes in text label image 2430. Similarly, outline image 2420 illustrates another version of the right image of text label image 2440 without the addition of text and/or images. Outline image 2420 presents a set of line drawings (e.g., empty boxes) corresponding to the text boxes in text label image 2440.

Outline image 2410 includes text boxes 2411, a right center edge 2412, and a dot 2414. Outline image 2420 includes text boxes 2421, a left center edge 2422, and a dot 2423. Text label image 2430 includes text boxes 2431, a right center edge 2432, a dot 2433, and dots 2434. Text label image 2440 includes text boxes 2441, a left center edge 2442, a dot 2443, and dots 2444. On the left image, text boxes 2411 show a set of empty text boxes corresponding to the text within text boxes 2431. Text boxes 2421 show how the text boxes of the label, corresponding to text boxes 2431, are drawn horizontally across the label, illustrating an example of the respective segments of text in a first image of a series of images, similar or identical to activity 701 (FIG. 7), described below. On the right image, text boxes 2421 show another set of empty text boxes corresponding to the text within text boxes 2441. Text boxes 2421 show how the text boxes of the label, corresponding to text boxes 2441, are drawn horizontally across the label, illustrating an example of the respective segments of text in a second image of a series of images, similar or identical to activity 701 (FIG. 7), described below.

The left image can be divided into four right edge centers (e.g., quarters) where each of the text boxes within a last quarter of the left image on the right side of the right edge center can be considered to be one or more eligible textboxes for merging. The right image also can be divided into four left edge centers (e.g., quarters) where each of the text boxes within the first quarter of the right image on the left side of the left edge center can be considered to be one or more eligible text boxes for merging.

In the left image, a right edge center 2412 of outline image 2410 is a vertical line drawn that partitions or divides the left image into a right portion, similar or identical to activity 702 (FIG. 7), described below. Right edge center 2412 can correspond to right edge center 2432. In the right image, a left edge center 2422 of outline image 2420 illustrates another vertical line that partitions or divides the right image into a left portion, similar or identical to activity 703 (FIG. 7), described below. Left edge center 2422 can correspond to left edge center 2442.

In the left image of outline image 2410, a dot 2414 marks a middle section of an eligible text box located on the right side of each text box for the left image that can be used as a point of reference to merge one eligible text box with another eligible text box. Dot 2414 can correspond to dot 2433. In the right image of outline image 2420, a dot 2423 marks a middle section of an eligible text box located on the left side of each text box for the right image that can be used as another point of reference to merge one eligible text box with another eligible text box. Dot 2423 can correspond to dot 2443.

Further, merge lines 2413 show an example of how an eligible text box from the left image can be mapped to other eligible text boxes in the right image, similar or identical to activity 704 (FIG. 7), described below. By merging partial text in an eligible text box on the left image with another partial text within another eligible text box on the right image, the merging algorithm, as described below, can merge one or more respective words to create lines of text of the prescription label. Each of the dots in each of the centers of each of the eligible text boxes can represent a respective point of reference for each box to be mapped together. For example, dot 2414 of an eligible text box on the left image maps to dot 2423 on another eligible text box on the right image. Dot 2433 of another eligible text box on the left image maps to dot 2443 on another eligible text box on the right image merging a set of words for sentence, as described below in greater detail in connection FIG. 26.

Returning to FIG. 4, in many embodiments, activity 406 can include determining a number of suitable text boxes (e.g., from 2411, 2421, 2431, 2441 (FIG. 24)), for a side by side comparison with one another. In several embodiments, activity 406 can include dividing both the left image of a first text box and the right image of a second text box where the two related images can be compared side by side, as shown in FIG. 24. Each image further can be divided into parts and/or partitions along a horizontal length of each image to match the content (e.g., text and/or image) of each text box on the left image with the content of the right image where the content of each image can be captured within more than one identified text box for each image, as shown in FIG. 24.

In some embodiments, activity 406 can include identifying the right edge centers (e.g., 2412, 2432) of each text box of the left image and identify the left edge centers (e.g., 2422, 2442) of each text box of the right image. In many embodiments, activity 406 can include determining a number of eligible text boxes can include analyzing a vertical section or boundary area of each portion of the prescription label to be compared. In several embodiments, dividing each image into 4 sections vertically can isolate each portion of the image into quarters for comparison. In some embodiments, analyzing a right quarter vertical section of the left image and a left quarter vertical section of the right image can allow each of the images to create a larger portion of the prescription label.

In a number of embodiments, right edge centers which lie in a last quarter of the left image (e.g., image 1) and left edge centers which lie in first quarter of the right image (e.g., image 2) can be considered as the eligible boxes for analysis of the context of the portions of the prescription label to merge. For example, merge the right quarter of the left and the left quarter of the right image to analyze a word or a sentence of the portion of the prescription label.

In several embodiments, each eligible box from the left image can be paired with matching merge candidates on the right image of the two portions of the prescription label. In some embodiments, each of the eligible merge candidates from the left image and the right image can be paired for a match. In various embodiments, a matching set of text boxes can be considered for a merge when the right edge center of a text box on the left image can be matched with the left edge center of a text box from the right image when left image is within a predetermined height from the right edge center.

In a number of embodiments, selecting the merge candidates on the right image for each eligible box of the left image includes generating a text similarity for each pair of eligible text boxes. In some embodiments, selecting the eligible text box includes (i) selecting the merge candidate with a maximum text similarity value with the left image text box and (ii) conducting a longest common substring merge with the text in the eligible text boxes. In several embodiments, a longest common substring merge includes merging the two textboxes by selecting characters from each text box on a planar portion of the non-planar surface and dropping the characters on the non-planar surface of the text box. In various embodiments, merging text boxes for each line of the prescription label can include several iterations of the merging algorithm repeated for each series for text boxes in the two or more images. For example, for each portion of the label compared, determine all of the right edge centers that are covered within the last quarter of the left image and all left edge centers that are covered within the first quarter of the right images.

Jumping ahead in the drawings, FIG. 7 illustrates a flow chart for activity 406 of merging, using a merging algorithm, the one or more respective words from the images to create lines of text. Activity 406 is merely exemplary and is not limited to the embodiments presented herein. Activity 406 can be employed in many different embodiments and/or examples not specifically depicted or described herein. In some embodiments, the procedures, the processes, and/or the activities of activity 406 can be performed in the order presented. In other embodiments, the procedures, the processes, and/or the activities of activity 406 can be performed in any suitable order. In still other embodiments, one or more of the procedures, the processes, and/or the activities of activity 406 can be combined or skipped.

In these or other embodiments, one or more of the activities of activity 406 can be implemented as one or more computing instructions configured to run at one or more processors and configured to be stored at one or more non-transitory computer-readable media. Such non-transitory computer-readable media can be part of a computer system such as prescription label scanner system 310 and/or web server 320. The processor(s) can be similar or identical to the processor(s) described above the respect to computer system 100 (FIG. 1).

In several embodiments, activity 406 can include an activity 701 of generating respective text boxes corresponding to the respective segments of text in a first image and a second image of the series of images. In some embodiments, the content of each of the text boxes can include a partial line of text and/or a partial image of an image, such as a name of a retail store, a prescription number, a phone number, and/or another suitable text line or image line of a prescription label. The first image can be similar or identical to outline image 2310 (FIG. 23) and/or and the second image (FIG. 23) can be similar or identical to outline image 2320.

In several embodiments, text boxes can be similar or identical to text boxes 2311 (FIG. 23), text boxes 2321 (FIG. 23), text boxes 2331 (FIG. 23), text boxes 2341 (FIG. 23), text box 2430 (FIG. 24, described below), and text area 2450 (FIG. 24, described below).

In many embodiments, activity 406 also can include an activity 702 of dividing the first image into at least a right portion. The right portion can be similar or identical to the portion of the left image (2410, 2430 (FIG. 24)) to the right of the right edge centers (e.g., 2412, 2432 (FIG. 24)).

In several embodiments, activity 406 further can include an activity 703 of dividing the second image into at least a left portion. The left portion can be similar or identical to the portion of the right image (2420, 2440 (FIG. 24)) to the right of the left edge centers (e.g., 2422, 2422 (FIG. 24)).

In some embodiments, activity 406 additionally can include an activity 704 of, for each text box of the respective text boxes in the right portion of the first image, selecting respective merge candidates from among the respective text boxes of the left portion of the right image. In various embodiments, determining a suitable merge candidate or candidate image from a first text box of the first image can include mapping (e.g., matching) similar content with a second text box of the second image. In several embodiments, identifying an image as a potential merge candidate with another adjacent image can include matching letters, numbers, and/or partial images that became illegible and/or distorted by the camera lens. For example, when the camera is aimed at a prescription label attached to a non-planar surface, such as a medication bottle, the characters or images that appear on the curved area of the label can become visually distorted when viewing the label in a two dimensional plane. In some embodiments, respective merge candidates can be similar or identical to merge candidates as shown in connection with dots 2434 (FIG. 24), dots 2444 (FIG. 24), text box 2630 (FIG. 26), and text area 2650 (FIG. 26), all as described further below. In a number of embodiments, activity 406 also can include an activity 705 of determining respective text similarities between the respective text boxes of the respective merge candidates and each text box in the right portion of the first image.

In several embodiments, activity 406 further can include an activity 706 of merging a respective merge candidate of the respective merge candidates having a highest one of the respective text similarities with the each text box using a longest common substring merging algorithm. In some embodiments, activity 706 can include comparing the content of two or more adjacent different images from a video of a prescription label, as shown in connection with FIG. 24 and FIG. 25 (described below). In various embodiments, the longest common substring merging algorithm also can be referred to a fuzzy merge algorithm and/or another suitable merge algorithm that can be implemented with a longest common substring merging technique. In several embodiments, mapping merge candidates in each of the text boxes to one another can include aligning a first merge candidate with a second merge candidate to form a word, a sentence, a sequence of numbers, and/or an image across a line of text of the prescription label.

Figure 25:
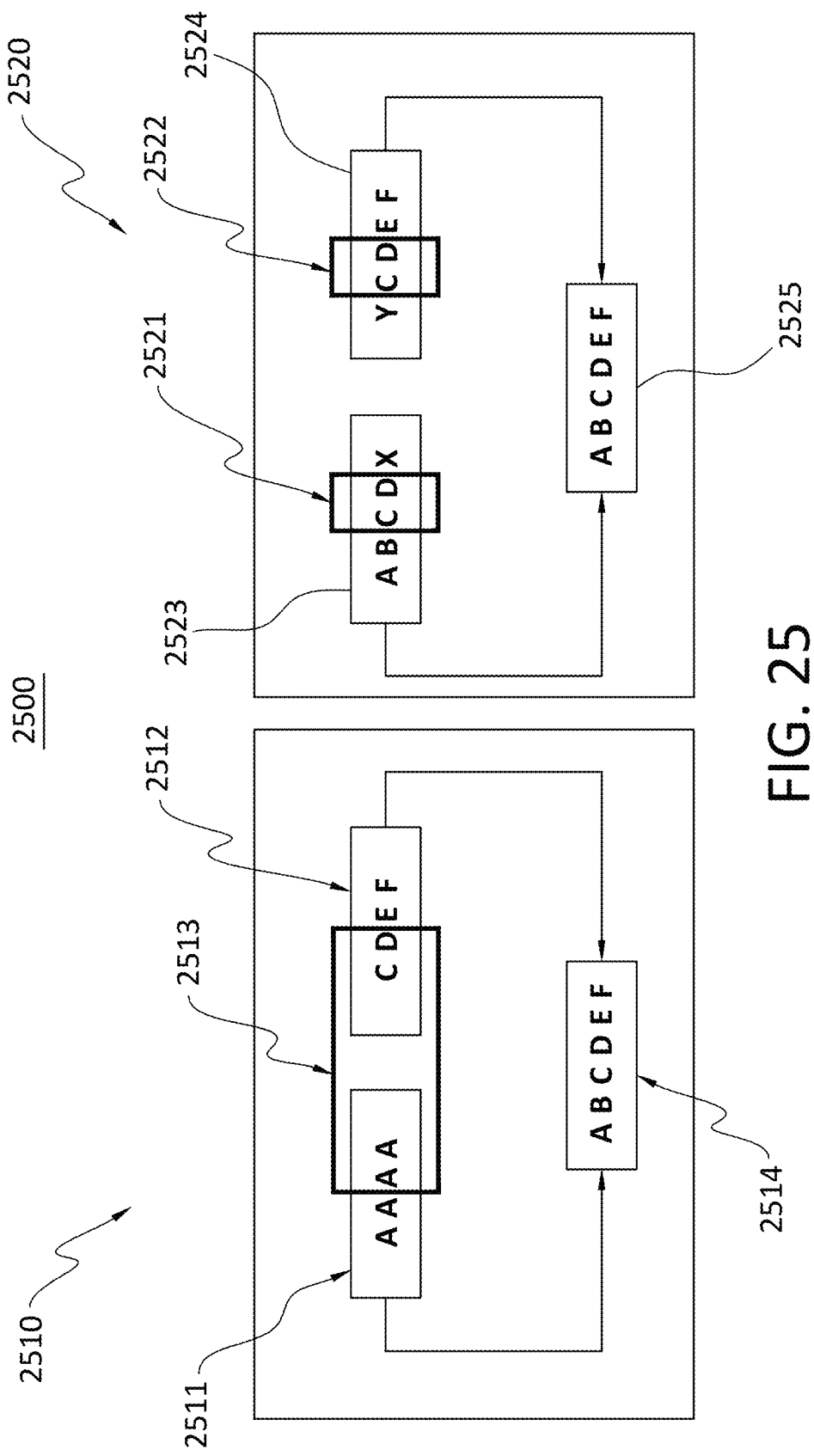
FIG. 25 illustrates sets of text boxes showing use of various longest common substring merging algorithms, according to the embodiment of FIG. 7.

Jumping ahead to the drawings, FIG. 25 illustrates a sets of text boxes 2500 showing use of various longest common substring merging algorithms. Sets of text boxes 2500 show examples of how to implement a longest common substring merge across two text boxes of a left image and a right image. A portion of text on each image can be obscured when viewed on a curved surface. Sets of text boxes 2500 can include a first set of text boxes 2510 and a second set of text boxes 2520.

First set of text boxes 2510 presents an example of a conventional method of mapping text across two text boxes of a left image and a right image. First set of text boxes 2510 can include a string box 2511, a string box 2512, a frame box 2513, and a result box 2514. First set of text boxes 2510 illustrates a comparison of the similar context in string box 2511 and string box 2512 as identified on two different frames from a video of a prescription label. Frame box 2513 illustrates a common substring of context identified for each frame of string box 2511 and string box 2512.

By combining the common substring of context with the context in string box 2511 and string box 2512, the full line of text of can be identified in result box 2514. For example, a context "ABCD" for string box 2511 and a context "CDEF" of string box 2512 can separately be identified on each of the two different frames from a video of a prescription label. Frame box 2513 identifies a common substring of context of "CD" for each frame of string box 2511 and string box 2512. By combining the common substring of context "CD" with the context in string box 2511 and string box 2512, the line of text of "ABCDEF" can be identified in result box 2514.

In some embodiments, the merging algorithm can include using a brute force approach (e.g., exhaustive search, generate and test) as a problem solving technique and comparing each text boxes of a left image and a right image, which can have a computational complexity of $O(n^2)$. In various embodiments, the brute force approach can be computationally expensive. In several embodiments, an optimized merging algorithm can decrease the computation complexity to $O(n \log n)$. In various embodiments, the optimized merging algorithm, as described below, can include an intelligent selection approach to make the system more robust and can increase the accuracy of the comparing the correct text boxes in the algorithm.

By contrast to the conventional mapping method of shown in first set of text boxes 2510, once merge candidates are mapped from a left image to a right image, a longest common substring merging algorithm can be used to merge text similarity across one merge candidate to another merge candidate. Second set of text boxes 2520 can include a selection box 2521, a selection box 2522, a string box 2523, a string box 2524 and a result box 2525.

Second set of text boxes 2520 can be processed by using the optimized algorithm of the merging algorithm, with computational complexity $O(n \log n)$ to locate the longest common substring merging for string box 2523 and string box 2524. In contrast to frame box 2513, longest common substring merging algorithm selects a portion of text in selection box 2521 and a similar portion of text in selection box 2522 as merge candidates to merge each text box with another text box. Selection box 2521 identifies a portion of text in string box 2523 within the text of the text box. Similarly, selection box 2522 identifies another portion of text in string box 2524 within the text of the text box. For example, string box 2523 can include "ABCDX" as the text within the text box and string box 2524 can include "YCDEF" as the text within the text box, where X and Y are placeholders for text on a curve that can be misread. In this example, the text "CD" is common to both sets of text in string box 2523 and string box 2524 where the text placeholder "X" in string box 2523 and the text placeholder "Y" in string box 2524 can have a high probability of being misread due to the curvature on a surface on the label. Based on the longest common substring of "CD", the text in string box 2523 and string box 2524 can be identify a merged text of "ABCDEF" of result box 2525.

Figure 26:
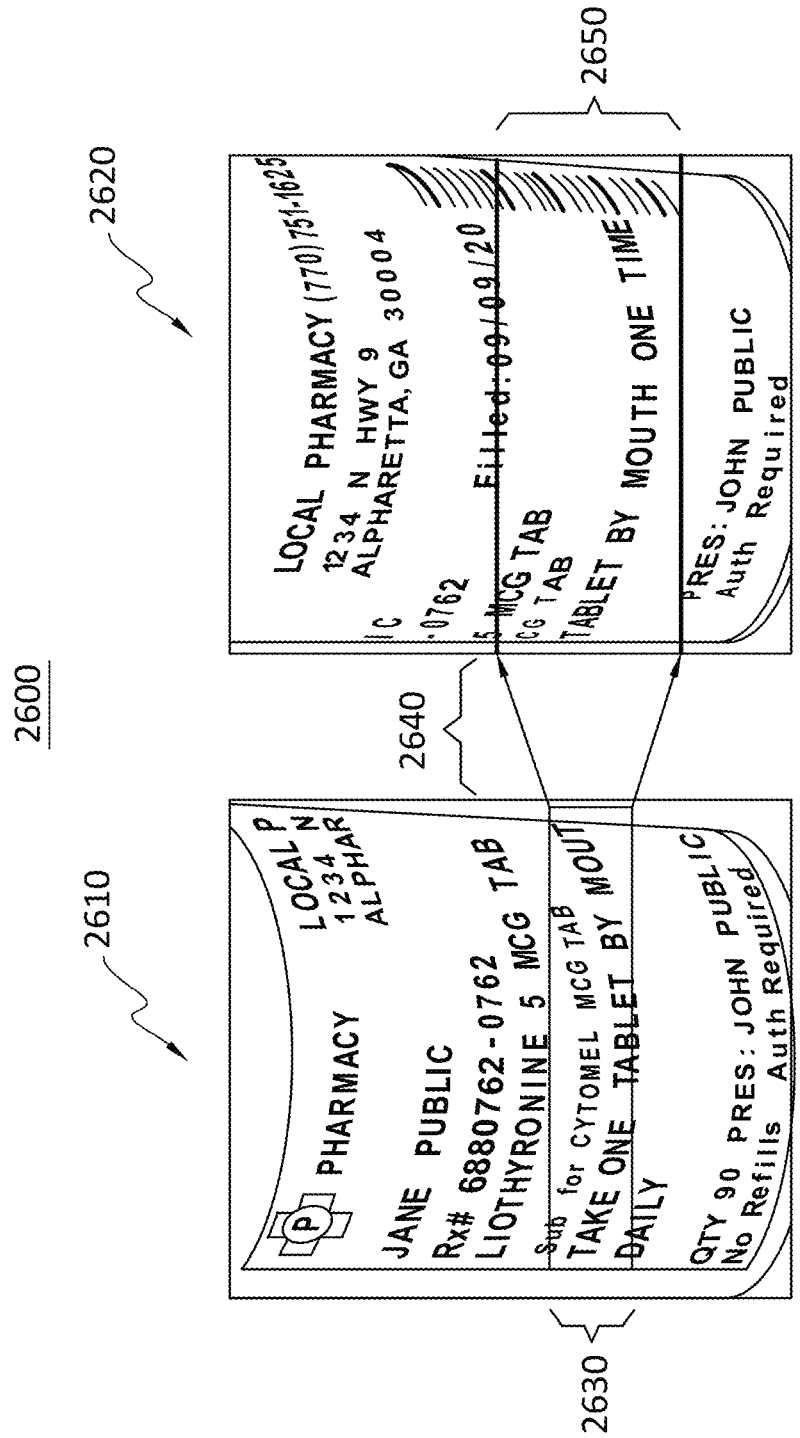
FIG. 26 illustrates a set of images use of a longest common substring merging algorithm, according to the embodiment of FIG. 7.

Turning ahead in the drawings, FIG. 26 illustrates a set of images 2600 showing use of a longest common substring merging algorithm. Set of images 2660 shows an example of how to merge a portion of partial text of a merge candidate text box of a left image to another portion of partial text in another merge candidate text box of a right image. Set of images 2600 includes a first sequence image 2610, a second sequence image 2620, a text box 2630, a matching sequence 2640, and a text area 2650.

In some embodiments, first sequence image 2610 illustrates a frame of a video showing a portion of the prescription label attached to a non-planar surface. In various embodiments, such a line of text can include prescription data such as an instruction of how to administer a prescription part of the sentence is obscured from view due to the curvature of a medication package. In several embodiments, second sequence image 2620 illustrates another frame of a video showing a rotated view of the prescription label attached to the non-linear surface. In some embodiments, such a line of text of how to administer the prescription can only be partially captured due to the curvature of the particular medication package. In various embodiments, text box 2630 is a portion of first sequence image 2610 with text content, e.g., "take one table by mou." In some embodiments, a matching sequence 2640 illustrates the process of text box 2630 of first sequence image 2610 to second sequence image 2620.

In a number of embodiments, a text area 2650 is a portion of second sequence image 2620 with text content, e.g., "by mouth one time." The longest common substring of text box 2630 and text area 2650 can be determined using these merge candidate for the line of text on the prescription label. For example, the context in a text box of a first image shows "take one tablet by mou," and the context a text box of a second image shows "by mouth one time." Using the merging algorithm to detect the longest common substring in both the first image and the second image associated with the line of text, the merged text can combine the context of a text line of a set of instructions for a user to identify the sentence: "take one tablet by mouth one time."

Turning back to FIG. 4, method 400 further can include an activity 407 of extracting, using a machine learning algorithm, prescription data associated with prescription data fields from the lines of text. In some embodiments, input for training data can be generated using historical data obtained from (1) prior prescription templates used by various medical dispensaries, (2) previous text data populated in text boxes from prescription data found on various rows of text boxes on prescription labels, and/or (3) previous words identified by the merging algorithm from the prescription labels. In several embodiments, output for the machine learning algorithm can include text, as structured data, that can match the original text of the original prescription. In many embodiments, the output of the structured data can be added to the training data as new training data. In various embodiments, updating the training data with the output of the structured data can increase the accuracy of the machine learning output performed in each new iteration using the machine learning algorithm over a predetermined number of iterations.

Jumping ahead in the drawings, FIG. 8 illustrates a flow chart for activity 407 of extracting, using a machine learning algorithm, prescription data associated with prescription data fields from the lines of text, according to an embodiment. Activity 407 is merely exemplary and is not limited to the embodiments presented herein. Activity 407 can be employed in many different embodiments and/or examples not specifically depicted or described herein. In some embodiments, the procedures, the processes, and/or the activities of activity 407 can be performed in the order presented. In other embodiments, the procedures, the processes, and/or the activities of activity 407 can be performed in any suitable order. In still other embodiments, one or more of the procedures, the processes, and/or the activities of activity 407 can be combined or skipped.

In these or other embodiments, one or more of the activities of activity 407 can be implemented as one or more computing instructions configured to run at one or more processors and configured to be stored at one or more non-transitory computer-readable media. Such non-transitory computer-readable media can be part of a computer system such as prescription label scanner system 310 and/or web server 320. The processor(s) can be similar or identical to the processor(s) described above the respect to computer system 100 (FIG. 1).

Referring to FIG. 8, activity 407 can include an activity 801 of receiving lines of text outputted by the merging algorithm. For example, the lines of text can be the output of activity 706 (FIG. 7).

In some embodiments, activity 407 also can include an activity 802 of extracting, using the machine learning algorithm, the prescription data from the lines of text based on the prescription data fields. In several embodiments, machine learning algorithms for an extractor can extract prescription data from lines of text and/or can include deep learning-based approaches to recognize: a named entity recognition, a regular expressions (e.g., prescription numbers), names of medications (e.g., prescription drugs), and/or another suitable word recognition. In a number of embodiments, deep learning-based approaches to recognize unstructured address strings for structured address components can be based on natural language processing (NLP) techniques. In some embodiments, a python library also can supplement the NLP processing technique for parsing the unstructured address strings into structured address components. In various embodiments, other machine learning techniques can include a Named-Entity Recognition (NER) using bidirectional long-short term memory (LS™) to classify a context of sentences. In some embodiments, machine learning algorithms for the extractor also can include a dictionary-based approach used to identify drug names by matching drugs with data from medical dictionaries. In some embodiments, the machine learning techniques further can include extracting structured data from templates of known prescription label formats.

In various embodiments, activity 407 further can include an activity 803 of populating each data field of the prescription data fields with the prescription data. Block 803 further can include the prescription data fields that can include at least one of (i) a prescription number, (ii) a pharmacy address, (iii) a medication, and/or another suitable prescription data field.

Figure 15:
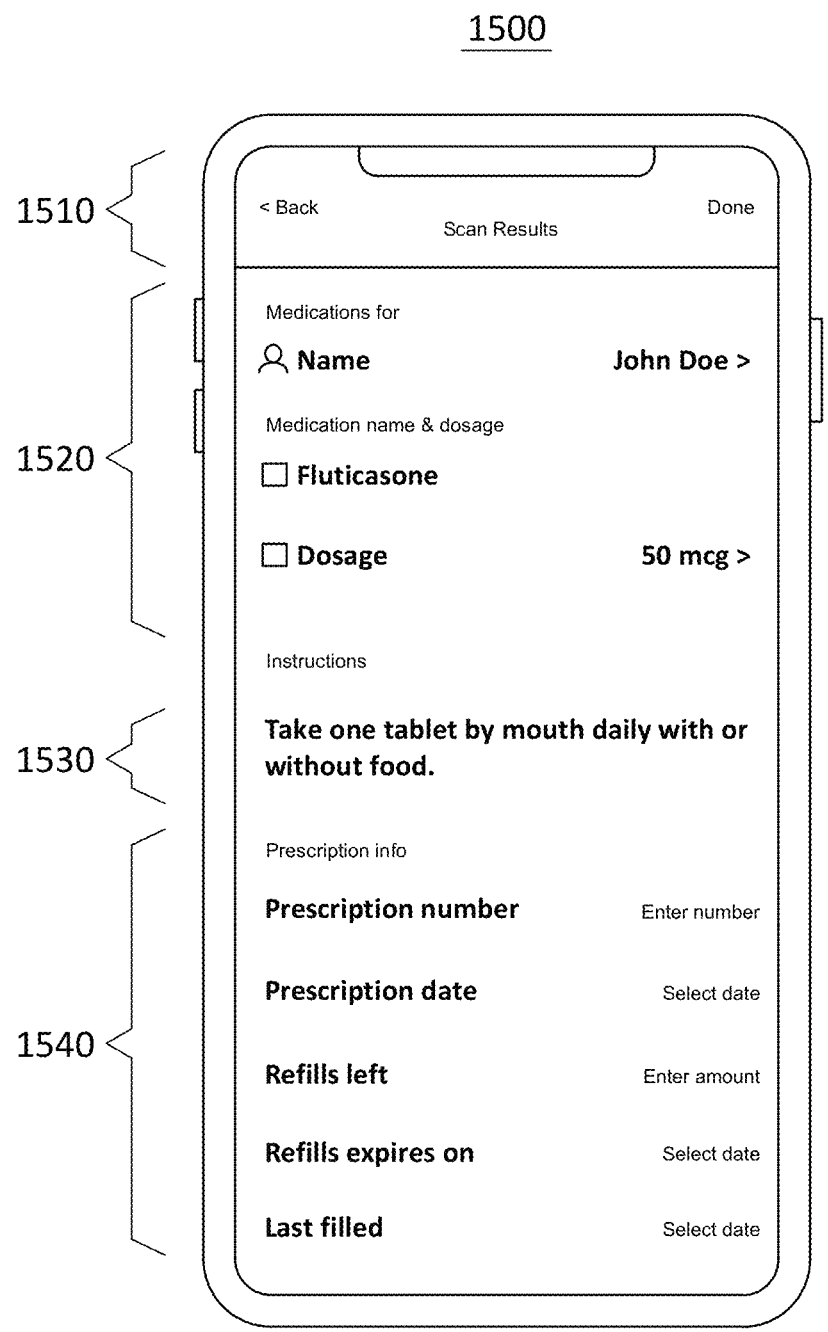
FIG. 15 illustrates an exemplary user interface display, according to an embodiment.

Jumping ahead in the drawings, FIG. 15 illustrates an exemplary user interface display 1500 showing an interactive screen display of a graphical user interface on a mobile device, according to another embodiment. In many embodiments, user interface display 1500 is merely exemplary, and embodiments of prescription label scanner for a medication package can be employed in many different embodiments or examples not specifically depicted or described herein. In a number of embodiments, user interface display 1500 can be an interactive webpage or a software app display to allow a user to retrieve and/or view the data extracted from the images of the video.

In some embodiments, user interface display 1500 can include a scanned results bar 1510, a prescription identification display 1520, a prescription instructions display 1530, and a prescription data display 1540.

In several embodiments, scanned results bar 1510 can display a title of the user interface display, can allow the user to return to a previous user interface screen and/or other captured images from a different prescription label, and/or can allow the user to end (e.g., done) the currently running user interface display by selecting a "back" button, icon, or another suitable return feature on the scanned results bar 1510.

In various embodiments, prescription identification display 1520 can display a list of information associated with the prescription and/or medication that can be extracted from the medication package, such as a name of a patient, a name of a medication prescribed to a patient, a dosage of the medication to be administered to the patient, and/or another suitable prescription data associated with a prescription medication.

In many embodiments, prescription instructions display 1530 can allow a user and/or a caregiver to view instructions, warnings, recommendations, and/or another suitable instruction associated with the prescription medication. Such instructions associated with the prescription medication for a user can be relayed to authorized persons and/or authorized retailers with the permission of the user. For example, a pharmacist can receive the instructions and other identifying information of the medication for the user to evaluate drug interactions, side-effects, and/or another suitable warning for a user.

In some embodiments, prescription data display 1540 can display one or more types of related prescription information extracted from a prescription label attached to a medication package such as a prescription number, a prescription date, a number of refills remaining on the prescription, an expiration date for a refill, a date when the prescription was last refilled, and/or another suitable type of prescription information.

Figure 16:
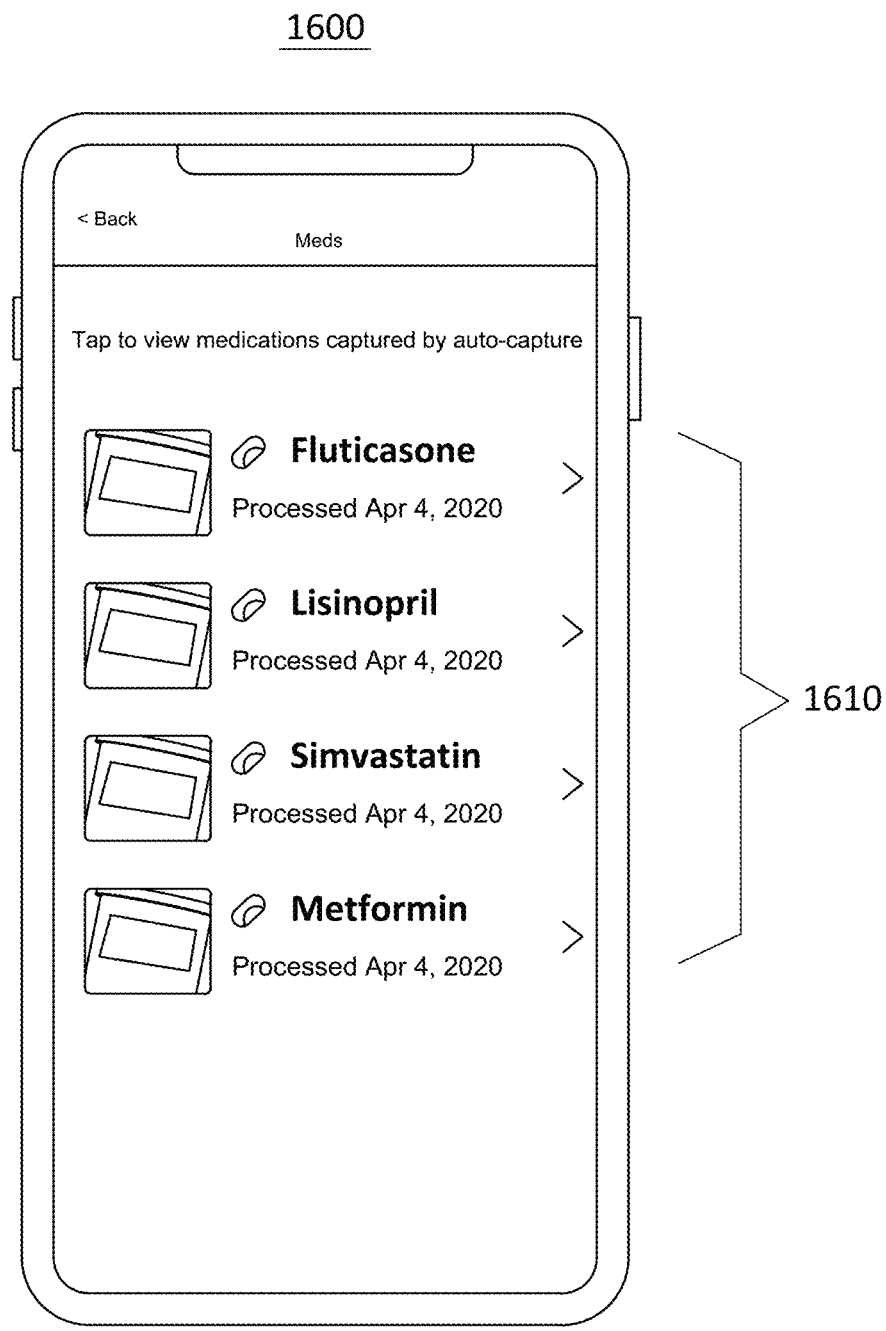
FIG. 16 illustrates an exemplary user interface display, according to an embodiment.

Proceeding to the next drawing, FIG. 16 illustrates an exemplary user interface display 1600 showing an interactive screen display of a graphical user interface on a mobile device, according to another embodiment. User interface display 1600 is merely exemplary, and embodiments of prescription label scanner for a medication package can be employed in many different embodiments or examples not specifically depicted or described herein. In a number of embodiments, user interface display 1600 can be an interactive webpage or a software app display to allow a user to retrieve and/or view a list of previously scanned prescriptions and/or medications of a user. In some embodiments, user interface display 1600 can include a list of prescription medications 1610.

In several embodiments, list of prescription medications 1610 can include a number of prescription medications for the user, which can include identifying information of a prescription information, for example, a date when the prescription label was processed. In some embodiments, list of prescription medications 1610 also can allow the user to select a prescription medication and retrieve, edit, and/or review additional information extracted from the prescription label displayed in another user interface display.

Figure 17:
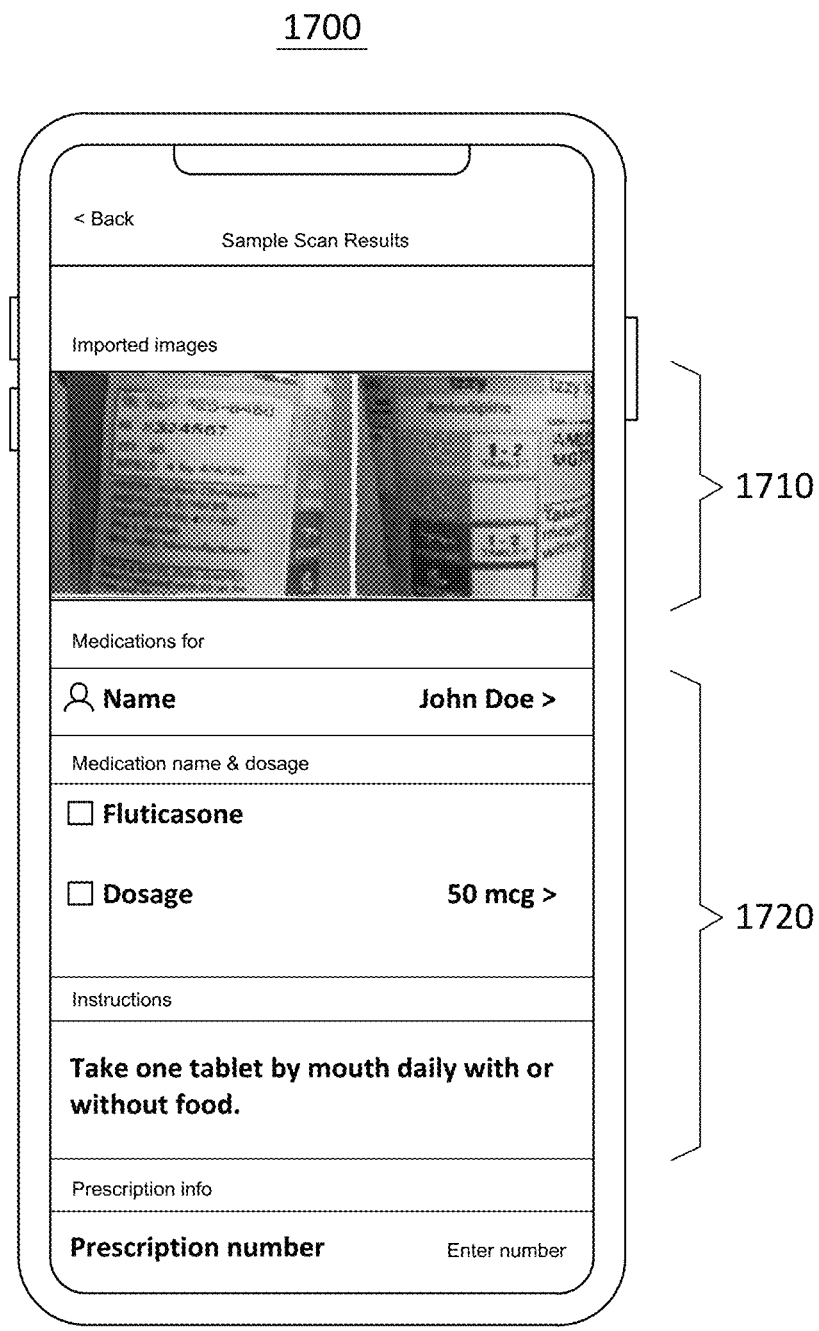
FIG. 17 illustrates an exemplary user interface display, according to an embodiment.

Turning ahead in the drawings, FIG. 17 illustrates an exemplary user interface display 1700 showing an interactive screen display of a graphical user interface on a mobile device, according to another embodiment. User interface display 1700 is merely exemplary, and embodiments of prescription label scanner for a medication package can be employed in many different embodiments or examples not specifically depicted or described herein. In a number of embodiments, user interface display 1700 can be an interactive webpage or a software app display to allow a user to retrieve or view (i) more than one image of the video adjacent to each other and (ii) the associated prescription data of the user.

In some embodiments, user interface display 1700 can include a scanned images interface display 1710 and a stored prescription medication data display 1720.

In several embodiments, scanned images interface display 1710 can allow the user to simultaneously view portions of the prescription label by retrieving stored images of the video. In some embodiments, scanned results bar 1710 can allow the user to return and/or retrieve previously stored prescription data from one or more other medication packages. In various embodiments, stored prescription medication data display 1720 can allow the user to concurrently view both the portions of the prescription label and the related prescription information associated with the portions of the prescription label.

Figure 9:
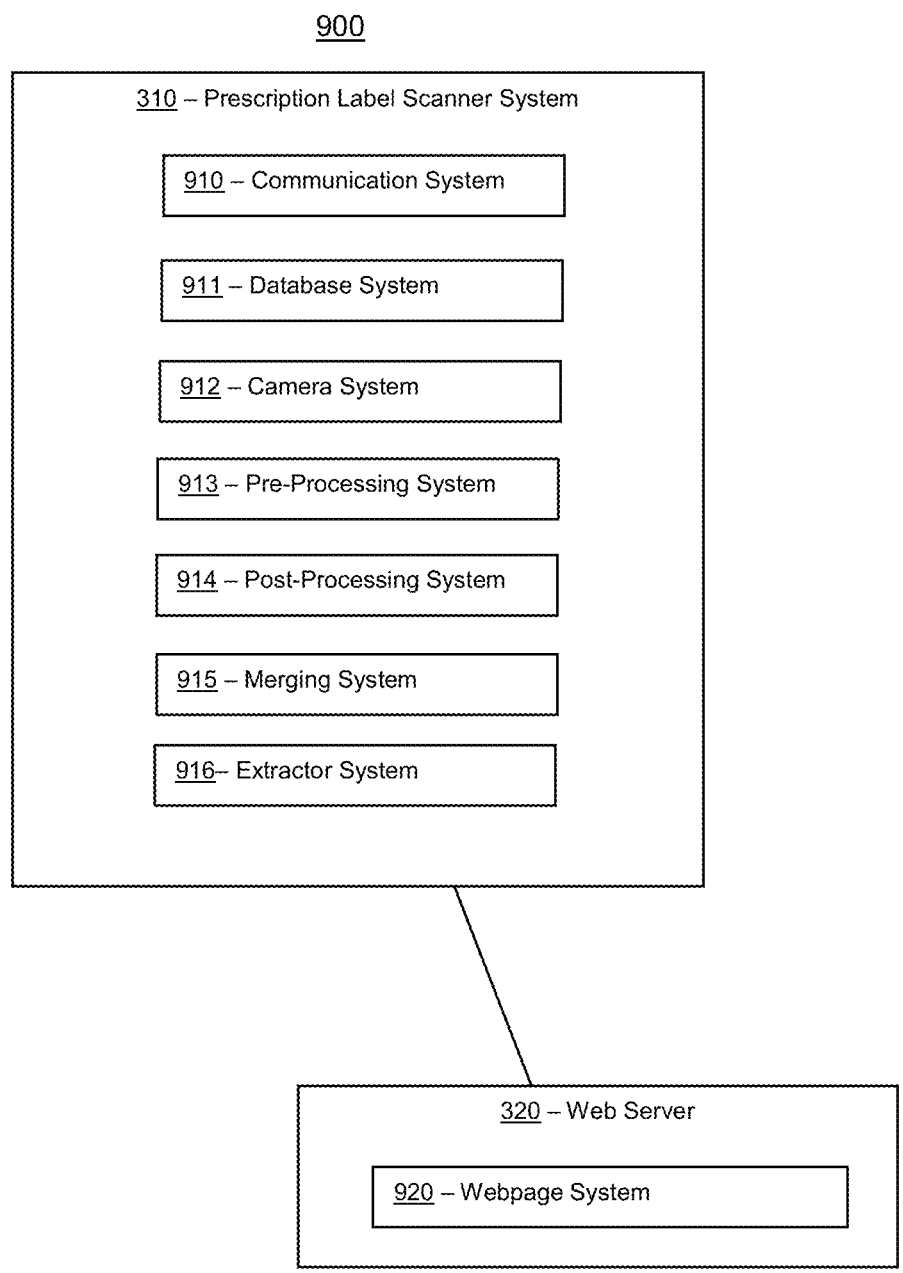
FIG. 9 illustrates a representative block diagram for a prescription label scanner system, according to the embodiment of FIG. 3.

Turning back to the drawings, FIG. 9 illustrates a block diagram of system 300, according to the embodiment shown in FIG. 3. Prescription label scanner system 310 and/or web server 320 are merely exemplary and are not limited to the embodiments presented herein. Prescription label scanner system 310 and/or web server 320 can be employed in many different embodiments or examples not specifically depicted or described herein. In some embodiments, certain elements or systems of prescription label scanner system 310 and/or web server 320 can perform various procedures, processes, and/or acts. In other embodiments, the procedures, processes, and/or acts can be performed by other suitable elements or systems. In many embodiments, the systems of prescription label scanner system 310 and/or web server 320 can be modules of computing instructions (e.g., software modules) stored at non-transitory computer readable media. In other embodiments, the systems of prescription label scanner system 310 and/or web server 320 can be implemented in hardware.

In many embodiments, prescription label scanner system 310 can include a communication system 910. In a number of embodiments, communication system 910 can at least partially perform activity 401 (FIG. 4) of facilitating display of instructions to a user interface of a mobile device of a user on how to rotate a medication package in front of a camera of the mobile device to capture a video of a rotated view of a non-planar surface of the medication package.

In several embodiments, prescription label scanner system 310 also can include a database system 911. In various embodiments, database system 911 can at least partially perform activity 502 (FIG. 5) of storing the one or more instructions comprise auto-capture tips.

In many embodiments, prescription label scanner system 310 further can include a camera system 912. In some embodiments, camera system 912 can at least partially perform activity 402 (FIG. 4) of capturing, using the camera, the video of the rotated view of the non-planar surface of the medication package, activity 501 (FIG. 5) of, upon initiating the camera on the mobile device of the user, triggering a window interface to appear on the user interface of the mobile device, wherein the window interface comprises an outline with boundary lines in which to capture the rotated view of the non-planar surface of the medication package, and/or activity 502 (FIG. 6) of, upon sensing that the camera is pointed at the medication package and that the medication package is viewed within the boundary lines of the outline of the window interface, automatically triggering an image box comprising one or more instructions to rotate the medication package while capturing the video of the rotated view of the medication package within the window interface, wherein the one or more instructions comprise auto-capture tips, and wherein the camera on the mobile device.

In some embodiments, prescription label scanner system 310 additionally can include a pre-processing system 913. In several embodiments, pre-processing system 913 can at least partially perform activity 403 (FIG. 4) of generating, using an input pre-processing algorithm, a series of images from the video, wherein each of the images shows a respective portion of the non-planar surface, activity 404 (FIG. 4) of converting respective segments of text in the respective portion of the non-planar surface within each of the images into respective machine-readable text data using an optical character recognition algorithm, activity 601 (FIG. 6) of mapping light and dark areas, using image inversion, to create a digital negative of an image of the video, activity 602 (FIG. 6) of adding, using dilation image processing, one or more first pixels to outer borders of elements of the image, activity 603 (FIG. 6) of removing, using erosion image processing, one or more second pixels from the outer borders of the elements of the image, activity 604 (FIG. 6) of modifying, using image rescaling, a size of the image to a different scale, activity 605 (FIG. 6) of assigning a thresholding value to one or more pixels of the image to contrast a background area of the image from a foreground area of the image, activity 606 (FIG. 6) of partitioning the image using image binarization processing to detect grey scale values of the image, activity 607 (FIG. 6) of defining borders of the image, activity 608 of rotating the image, activity 609 (FIG. 6) of partitioning the image using image binarization processing to detect grey scale values of the image, and/or activity 610 (FIG. 6) of de-warping the image to remove warp distortion of the image.

In a number of embodiments, prescription label scanner system 310 further can include a post-processing system 914. In some embodiments, post-processing system 914 can at least partially perform activity 405 (FIG. 4) of recognizing, using an output post-processing algorithm, one or more respective words from the respective machine-readable text data corresponding to the respective segments of text in the respective portion of the non-planar surface within each of the images.

In various embodiments, prescription label scanner system 310 also can include a merging system 915 can at least partially perform activity 406 (FIG. 4) of merging, using a merging algorithm, the one or more respective words from the images to create lines of text, activity 701 (FIG. 7) of generating respective text boxes corresponding to the respective segments of text in a first image and a second image of the series of images, activity 702 (FIG. 7) of dividing the first image into at least a right portion, activity 703 (FIG. 7) of dividing the second image into at least a left portion, activity 704 (FIG. 7) of, for each text box of the respective text boxes in the right portion of the first image, selecting respective merge candidates from among the respective text boxes of the left portion of the right image, activity 705 (FIG. 7) of determining respective text similarities between the respective text boxes of the respective merge candidates and each text box in the right portion of the first image, and/or activity 706 (FIG. 7) of merging a respective merge candidate of the respective merge candidates having a highest one of the respective text similarities with the each text box using a longest common substring merging algorithm.

In many embodiments, prescription label scanner system 310 further can include an extractor system 916. In some embodiments, extractor system 916 can at least partially perform activity 407 (FIG. 4) of extracting, using a machine learning algorithm, prescription data associated with prescription data fields from the lines of text, activity 801 (FIG. 8) of receiving lines of text outputted by the merging algorithm, activity 802 (FIG. 8) of extracting, using the machine learning algorithm, the prescription data from the lines of text based on the prescription data fields, and/or activity 803 (FIG. 8) of populating each data field of the prescription data fields with the prescription data.

In several embodiments, web server 320 can include a webpage system 920, which can display webpages, mobile application screens, or other pages to the user.

Figure 18:
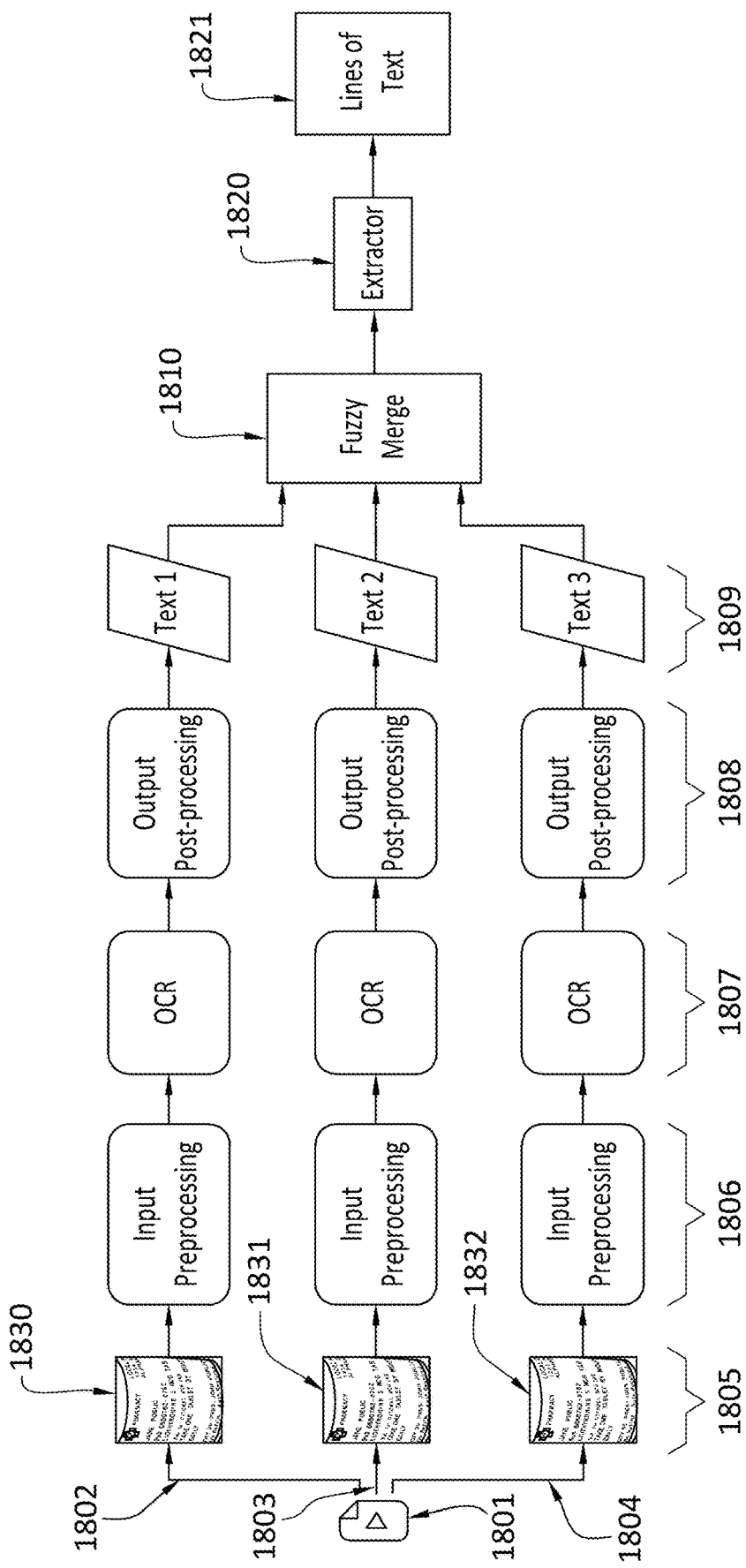
FIG. 18 illustrates a flow chart for a method, according to another embodiment.

Jumping ahead in the drawings, FIG. 18 illustrates a flow chart for a method 1800, according to another embodiment. Method 1800 illustrates how a parallel processing can be used to process a video of a prescription label to generate lines of text extracted from each selected frame of the video. Method 1800 can be similar or identical to method 400 (FIG. 4). Method 1800 can be employed in many different embodiments and/or examples not specifically depicted or described herein. In some embodiments, the procedures, the processes, and/or the activities of method 1800 can be performed in the order presented or in parallel. In other embodiments, the procedures, the processes, and/or the activities of method 1800 can be performed in any suitable order. In still other embodiments, one or more of the procedures, the processes, and/or the activities of method 1800 can be combined or skipped. In several embodiments, system 300 (FIG. 3) can be suitable to perform method 1800 and/or one or more of the activities of method 1800.

In these or other embodiments, one or more of the activities of method 1800 can be implemented as one or more computing instructions configured to run at one or more processors and configured to be stored at one or more non-transitory computer-readable media. Such non-transitory computer-readable media can be part of a computer system such as prescription label scanner 310 and/or web server 320. The processor(s) can be similar or identical to the processor(s) described above with respect to computer system 100 (FIG. 1).

In several embodiments, method 1800 illustrates an example of how a set of a series of frames from a video frames can be processed in parallel, where each video frame is a rotated view of a previous video frame or a subsequent video frame. In some embodiments, method 1800 can include (i) a set of processes 1802-1804 for processing frames 1830-1832, respectively, of a video 1801 and (ii) a set of activities 1056-1809 used in each of the processes (e.g., 1802-1804).

In many embodiments, method 1800 can begin with capturing video 1801 of a rotated view of a prescription label affixed to a medication package. In several embodiments, frames 1805 (e.g., frame 1830, frame 1831, and frame 1832) from video 1801 with some overlap in each subsequent frame to encompass the entirety of, or a relevant portion of, the prescription label when viewed side by side. For example, relevant frames can be selected from among other rotated frames capturing a left side view, middle side view, and a right side view to cover the entire prescription label. In some embodiments, each of the individual images of the video can include a series of frames and/or images showing a rotated view and/or a different portion of the prescription label as captured in the video. In several embodiments, each frame of the video can depict or show a different portion of the prescription label captured in each frame.

In several embodiments, video 1801 can include images of a planar surface, an oversized planar surface, multiple planar surfaces, and/or other surfaces that cannot be completely captured in a single frame of a video. Examples of the surfaces can include a billboard sign or a store front window. For example, a user riding on a streetcar can capture a video of a billboard sign while the streetcar passes the sign. In such an example, the entire text on the billboard cannot be captured in a single video frame. Such images captured in a video also can be processed by method 1800.

In various embodiments, method 1800 can process multiple frames of the video in parallel. In many embodiments each frame of the video can capture a particular portion of a prescription label that can include a partial text data and/or a partial image data. In several embodiments, frames 1805 can be selecting from portions of the rotated view of the prescription label, and such a selection of each portion of the rotated view can be similar or identical to the procedures, processes, and/or activity of 402 (FIG. 4). In various embodiments, the images selected can include adjacent portions of the prescription label to display the entire text and/or images of the prescription data, for example a label attached to a rounded medication bottle. In many embodiments, frame 1805 can include images and/or visual perspectives of a portion of the rotated view of the prescription label.

For example, frame 1830 can be a first image showing a first portion of the prescription label selected from the video of the rotated view of the prescription label, frame 1831 can be second image rotated by a predetermined degree of rotation showing a second portion of the prescription label, and frame 1832 of a third image rotated by a predetermined degree of rotation showing a third portion of the prescription label.

In many embodiments, method 1800 can include, for each process (e.g., 1802-1804), an activity 1806 of input processing by processing each rotated view of an image taken from the video by using one or more approaches and/or techniques of input processing, such input processing approaches and/or techniques can be similar or identical to the procedures, processes, and/or activities of 601-610 (FIG. 6). Each image of a respective portion of the prescription label can be processed using the one or more input processing methods to create clear and legible characters and/or images to be read using an OCR technique. For example, frame 1830 in process 1802 can be processed using one or more of the input processing techniques shown in input processing column 1806, such as image inversion 601 (FIG. 6) and dilation image processing 602 (FIG. 6). In many embodiments, each frame can undergo multiple input processes to generate a legible and/or quality output in preparation for an OCR process and/or any other character recognition technique to read each character and/or image of the frame.

In various embodiments, method 1800 can include, for each process (e.g., 1802-1804), an activity 1807 of OCR by recognizing and/or translating the characters and/or images from a portion of the frame of a video. In several embodiments, once the characters and/or image has been recognized and/or translated as machine-readable text, the output of the OCR process can be input into the next sequence of output post-processing.

In many embodiments, method 1800 can include, for each process (e.g., 1802-1804), an activity 1808 of output post-processing by processing the output of the machine-readable text and processing into segments of text recognized in the portion of the frame of the video.

In several embodiments, method 1800 can include, for each process (e.g., 1802-1804), an activity of 1809 of text box processing by gathering the text segments of the output post-processing algorithm in preparation to merge the text segments using a merging algorithm.

In a number of embodiments, method 1800 can include an activity 1810 of fuzzy merging the text segments from the frames from the processes (e.g., 1802-1804) into words and/or sentences.

In some embodiments, method 1800 can include an activity 1820 of extracting by identifying words and/or sentences output from the merging algorithm across the portions of the label to merge the portions into lines and/or sentences to generate lines of text from the prescription label across the portions of the frames of the video from the rows of the flow chart into lines of text.

Various embodiments can include a system including one or more processors and one or more non-transitory computer-readable media storing computing instructions configured to run on the one or more processors and perform certain acts. The acts can include facilitating display of instructions to a user interface of a mobile device of a user. The display can include instructions on how to rotate a medication package in front of a camera of the mobile device to capture a video of a rotated view of a non-planar surface of the medication package. The acts also can include capturing, using the camera, the video of the rotated view of the non-planar surface of the medication package. The acts further can include generating, using an input pre-processing algorithm, a series of images from the video. Each of the images in the series of images can show a respective portion of the non-planar surface. The acts also can include converting respective segments of text in the respective portion of the non-planar surface within each of the images into respective machine-readable text data using an optical character recognition algorithm. The acts further can include recognizing, using an output post-processing algorithm, one or more respective words from the respective machine-readable text data. The machine-readable text data can correspond to the respective segments of text in the respective portion of the non-planar surface within each of the images. The acts additionally further can include merging, using a merging algorithm, the one or more respective words from the images to create lines of text. The acts also can include extracting, using a machine learning algorithm, prescription data associated with prescription data fields from the lines of text.

A number of embodiments can include a method being implemented via execution of computing instructions configured to run at one or more processors and stored at one or more non-transitory computer-readable media. The method can include facilitating display of instructions to a user interface of a mobile device of a user. The display can include instructions on how to rotate a medication package in front of a camera of the mobile device to capture a video of a rotated view of a non-planar surface of the medication package. The method also can include capturing, using the camera, the video of the rotated view of the non-planar surface of the medication package. The method further can include generating, using an input pre-processing algorithm, a series of images from the video. Each of the images in the series of images can show a respective portion of the non-planar surface. The method also can include converting respective segments of text in the respective portion of the non-planar surface within each of the images into respective machine-readable text data using an optical character recognition algorithm. The method further can include recognizing, using an output post-processing algorithm, one or more respective words from the respective machine-readable text data. The machine-readable text data can correspond to the respective segments of text in the respective portion of the non-planar surface within each of the images. The method additionally further can include merging, using a merging algorithm, the one or more respective words from the images to create lines of text. The method also can include extracting, using a machine learning algorithm, prescription data associated with prescription data fields from the lines of text.

Conventional approaches of capturing a panoramic view or views of an object where the object is stationary and the camera moves can present several challenges to capture accurate data particularly when the object is not a flat object or where a label containing the prescription data is attached beyond a side of the flat object that cannot be entirely viewed on any side of the flat object. Such challenges can include not capturing a key datum or a key character of a word or phrase of the specific prescription information written on a label attached to a non-planar surface. For example, missing a character of a word on a prescription label can record an incorrect medication as prescribed or the wrong instructions on how or when to take medication or an incorrect refill date and/or expiration date of the medication and/or another suitable mistake. Such challenges have been linked to capturing low accuracy and/or mistakes related to a prescription medication when all of the prescription data cannot be reliably captured. Additionally, such conventional approaches can include a process to convert the series of image into a single image using image stitching. Conventional methods of image stitching a series of images can include visually selecting key points on several images where the key points can overlap by approximately 30% of the image to join the portions of the label together. Extracting information from the 30% of each image stitched together also can result in missing portions of the text of a prescription data that can be inadvertently omitted from the series of images.

Generally, multiple medications for a single user can be distributed in different form factors (e.g., medication packages) and/or from different retailers, such as pharmacies, and/or from different methods of delivery, such as a delivery service, mail, and/or other suitable delivery services. In many embodiments, a prescription label scanner can be advantageous in that it can be used to correctly extract correct information from text located over a curved object. Such advantages can allow users to capture prescription data on a label of attached to a variety of objects or packages, such as a round bottle, a tube, a hexagonal bottle, a box where the label wraps around the object and/or from another suitable medication package by capturing a video of a panoramic view of the package.

In various embodiments, an advantage of using the prescription label scanner can be found in the user interface assist feature that allows the user to receive feedback in real-time while the object is rotated in front of the camera. The specific instructions can include modifying a position or view of the object, zooming in or out from the camera lens, lighting, focus and/or another suitable instruction. Extracting structured prescription data from a video (e.g., a series of images) taken of the prescription label can be used for planar surfaces (e.g., flat) and/or non-planar surfaces (e.g., rounded, hexagonal, tubular). In several embodiments, the prescription label scanner can analyze the rotated video using an OCR Service API approach in real-time or on the fly.

In many embodiments, the techniques described herein can provide several technological improvements. In some embodiments, the techniques described herein can provide for automatically determining how to capture the data on a prescription label attached to a curved surface. In a number of embodiments, the techniques described herein can provide for implementing corrective imaging techniques for each frame of the video. In many embodiments, the techniques described herein can beneficially make determinations based on real-time information that describes the current prescription data of a medication of a user. In a number of embodiments, the techniques described herein can advantageously enable input pre-processing, such as activity 403 (FIGS. 4 and 6), which can beneficially result in a reduction in image error and incorrect prescription data.

Although automatically extracting prescription data from a label on a prescription package using a prescription label scanner has been described with reference to specific embodiments, it will be understood by those skilled in the art that various changes may be made without departing from the spirit or scope of the disclosure. Accordingly, the disclosure of embodiments is intended to be illustrative of the scope of the disclosure and is not intended to be limiting. It is intended that the scope of the disclosure shall be limited only to the extent required by the appended claims. For example, to one of ordinary skill in the art, it will be readily apparent that any element of FIGS. 1-26 may be modified, and that the foregoing discussion of certain of these embodiments does not necessarily represent a complete description of all possible embodiments. For example, one or more of the procedures, processes, or activities of FIGS. 4-8 and 18 may include different procedures, processes, and/or activities and be performed by many different modules, in many different orders, and/or one or more of the procedures, processes, or activities of FIGS. 4-8 and 18 may include one or more of the procedures, processes, or activities of another different one of FIGS. 4-8 and 18. As another example, the systems within prescription label reader 310 and/or webserver 320 (FIG. 9 can be interchanged or otherwise modified).

Replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:
1. A system comprising:
one or more processors; and
one or more non-transitory computer-readable media storing computing instructions configured to run on the one or more processors and perform:

facilitating display of instructions to a user interface of a mobile device of a user on how to rotate a medication package in front of a camera of the mobile device to capture a video of a rotated view of a non-planar surface of the medication package;

capturing, using the camera, the video of the rotated view of the non-planar surface of the medication package;

generating, using an input pre-processing algorithm, a series of images from the video, wherein each of the images shows a respective portion of the non-planar surface;

converting respective segments of text in the respective portion of the non-planar surface within each of the images into respective machine-readable text data using an optical character recognition algorithm;

recognizing, using an output post-processing algorithm, one or more respective words from the respective machine-readable text data corresponding to the respective segments of text in the respective portion of the non-planar surface within each of the images;

merging, using a merging algorithm, the one or more respective words from the images to create lines of text; and extracting, using a machine learning algorithm, prescription data associated with prescription data fields from the lines of text.

2. The system of claim 1, wherein facilitating display of the instructions to the user interface of the mobile device of the user comprises:

upon initiating the camera on the mobile device of the user, triggering a window interface to appear on the user interface of the mobile device, wherein the window interface comprises an outline with boundary lines in which to capture the rotated view of the non-planar surface of the medication package; and upon sensing that the camera is pointed at the medication package and that the medication package is viewed within the boundary lines of the outline of the window interface, automatically triggering an image box comprising one or more instructions to rotate the medication package while capturing the video of the rotated view of the medication package within the window interface, wherein the one or more instructions comprise auto-capture tips, and wherein the camera on the mobile device remains in a substantially stationary position while the medication package is rotated.

3. The system of claim 1, wherein generating, using the input pre-processing algorithm, the series of images from the video comprises at least one of:

mapping light and dark areas, using image inversion, to create a digital negative of an image of the video;

adding, using dilation image processing, one or more first pixels to outer borders of elements of the image;

removing, using erosion image processing, one or more second pixels from the outer borders of the elements of the image;

modifying, using image rescaling, a size of the image to a different scale;

assigning a thresholding value to one or more pixels of the image to contrast a background area of the image from a foreground area of the image;

partitioning the image using image binarization processing to detect grey scale values of the image; or defining borders of the image.

4. The system of claim 3, wherein generating, using the input pre-processing algorithm, the series of images from the video further comprises at least one of:

rotating the image;

deskewing the image to align the image horizontally and vertically; or de-warping the image to remove warp distortion of the image.

5. The system of claim 1, wherein recognizing, using the output post-processing algorithm, one or more respective words from the respective machine-readable text data comprises:

segmenting the machine-readable text data to recognize the one or more respective words based at least in part on customized receipt codes.

6. The system of claim 5, wherein recognizing, using the output post-processing algorithm, one or more respective words from the respective machine-readable text data further comprises:

segmenting the machine-readable text data to recognize the one or more respective words based at least in part on one or more customized medical dictionaries.

7. The system of claim 1, wherein merging, using the merging algorithm, the one or more respective words from the images to create lines of text comprises:

generating respective text boxes corresponding to the respective segments of text in a first image and a second image of the series of images;

dividing the first image into at least a right portion; and dividing the second image into at least a left portion.

8. The system of claim 7, wherein merging, using the merging algorithm, the one or more respective words from the images to create lines of text further comprises:

for each text box of the respective text boxes in the right portion of the first image, selecting respective merge candidates from among the respective text boxes of the left portion of the second image;

determining respective text similarities between the respective text boxes of the respective merge candidates and each text box in the right portion of the first image; and merging a respective merge candidate of the respective merge candidates having a highest one of the respective text similarities with the each text box using a longest common substring merging algorithm.

9. The system of claim 8, wherein the longest common substring merging algorithm comprises:

merging a respective longest common substring of the respective merge candidate with the longest common substring of the each text box to a respective line of text across the first image and the second image.

10. The system of claim 1, wherein extracting, using the machine learning algorithm, the prescription data comprises:

receiving lines of text outputted by the merging algorithm;

extracting, using the machine learning algorithm, the prescription data from the lines of text based on the prescription data fields;

populating each data field of the prescription data fields with the prescription data, wherein the prescription data fields comprise at least one of:
a prescription number;
a pharmacy address; or
a medication.

11. A method implemented via execution of computing instructions configured to run on one or more processors and stored at one or more non-transitory computer-readable media, the method comprising:
   facilitating display of instructions to a user interface of a mobile device of a user on how to rotate a medication package in front of a camera of the mobile device to capture a video of a rotated view of a non-planar surface of the medication package;
   capturing, using the camera, the video of the rotated view of the non-planar surface of the medication package;
   generating, using an input pre-processing algorithm, a series of images from the video, wherein each of the images shows a respective portion of the non-planar surface;
   converting respective segments of text in the respective portion of the non-planar surface within each of the images into respective machine-readable text data using an optical character recognition algorithm;
   recognizing, using an output post-processing algorithm, one or more respective words from the respective machine-readable text data corresponding to the respective segments of text in the respective portion of the non-planar surface within each of the images;
   merging, using a merging algorithm, the one or more respective words from the images to create lines of text; and
   extracting, using a machine learning algorithm, prescription data associated with prescription data fields from the lines of text.

12. The method of claim 1, wherein facilitating display of the instructions to the user interface of the mobile device of the user comprises:
   upon initiating the camera on the mobile device of the user, triggering a window interface to appear on the user interface of the mobile device, wherein the window interface comprises an outline with boundary lines in which to capture the rotated view of the non-planar surface of the medication package; and
   upon sensing that the camera is pointed at the medication package and that the medication package is viewed within the boundary lines of the outline of the window interface, automatically triggering an image box comprising one or more instructions to rotate the medication package while capturing the video of the rotated view of the medication package within the window interface, wherein the one or more instructions comprise auto-capture tips, and wherein the camera on the mobile device remains in a substantially stationary position while the medication package is rotated.

13. The method of claim 11, wherein generating, using the input pre-processing algorithm, the series of images from the video comprises at least one of:
   mapping light and dark areas, using image inversion, to create a digital negative of an image of the video;
   adding, using dilation image processing, one or more first pixels to outer borders of elements of the image;
   removing, using erosion image processing, one or more second pixels from the outer borders of the elements of the image;
   modifying, using image rescaling, a size of the image to a different scale;
   assigning a thresholding value to one or more pixels of the image to contrast a background area of the image from a foreground area of the image;
   partitioning the image using image binarization processing to detect grey scale values of the image; or
   defining borders of the image.

14. The method of claim 13, wherein generating, using the input pre-processing algorithm, the series of images from the video further comprises at least one of:
   rotating the image;
   deskewing the image to align the image horizontally and vertically; or
   de-warping the image to remove warp distortion of the image.

15. The method of claim 11, wherein recognizing, using the output post-processing algorithm, one or more respective words from the respective machine-readable text data comprises:
   segmenting the machine-readable text data to recognize the one or more respective words based at least in part on customized receipt codes.

16. The method of claim 15, wherein recognizing, using the output post-processing algorithm, one or more respective words from the respective machine-readable text data further comprises:
   segmenting the machine-readable text data to recognize the one or more respective words based at least in part on one or more customized medical dictionaries.

17. The method of claim 11, wherein merging, using the merging algorithm, the one or more respective words from the images to create lines of text comprises:
   generating respective text boxes corresponding to the respective segments of text in a first image and a second image of the series of images;
   dividing the first image into at least a right portion; and
   dividing the second image into at least a left portion.

18. The method of claim 17, wherein merging, using the merging algorithm, the one or more respective words from the images to create lines of text further comprises:
   for each text box of the respective text boxes in the right portion of the first image, selecting respective merge candidates from among the respective text boxes of the left portion of the second image;
   determining respective text similarities between the respective text boxes of the respective merge candidates and each text box in the right portion of the first image; and
   merging a respective merge candidate of the respective merge candidates having a highest one of the respective text similarities with the each text box using a longest common substring merging algorithm.

19. The method of claim 18, wherein the longest common substring merging algorithm comprises:
   merging a respective longest common substring of the respective merge candidate with the longest common substring of the each text box to a respective line of text across the first image and the second image.

20. The method of claim 11, wherein extracting, using the machine learning algorithm, the prescription data comprises:
   receiving lines of text outputted by the merging algorithm;
   extracting, using the machine learning algorithm, the prescription data from the lines of text based on the prescription data fields;
   populating each data field of the prescription data fields with the prescription data,
   wherein the prescription data fields comprise at least one of:
      a prescription number;
      a pharmacy address; or
      a medication.

* * * * *